(12) United States Patent
Marker et al.

(10) Patent No.: US 12,410,371 B2
(45) Date of Patent: *Sep. 9, 2025

(54) PROCESSES AND SYSTEMS FOR REFORMING OF METHANE AND LIGHT HYDROCARBONS TO LIQUID HYDROCARBON FUELS

(71) Applicant: GTI Energy, Des Plaines, IL (US)

(72) Inventors: Terry Marker, Park Ridge (IL);
Martin B. Linck, Wilmette, IL (US);
Jim Wangerow, Oak Park, IL (US);
Pedro Ortiz-Toral, Wheeling, IL (US)

(73) Assignee: GTI Energy, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/136,031

(22) Filed: Apr. 18, 2023

(65) Prior Publication Data

US 2023/0348800 A1 Nov. 2, 2023

Related U.S. Application Data

(60) Continuation of application No. 16/928,096, filed on Jul. 14, 2020, now Pat. No. 11,667,853, which is a
(Continued)

(51) Int. Cl.
*C10G 50/00* (2006.01)
*B01D 3/06* (2006.01)
(Continued)

(52) U.S. Cl.
CPC ............... *C10G 50/00* (2013.01); *B01D 3/06* (2013.01); *B01D 3/143* (2013.01); *C07C 1/04* (2013.01);
(Continued)

(58) Field of Classification Search
None
See application file for complete search history.

(56) References Cited

U.S. PATENT DOCUMENTS

| 3,531,396 | A | 9/1970 | Messing et al. |
| 3,700,585 | A | 10/1972 | Chen et al. |
| | | (Continued) | |

FOREIGN PATENT DOCUMENTS

| CN | 1184144 A | 6/1998 |
| CN | 102872905 A | 1/2013 |
| | (Continued) | |

OTHER PUBLICATIONS

Dec. 12, 2023—(EP) Partial European Search Report—App EP23196545.0.
(Continued)

*Primary Examiner* — Tam M Nguyen
(74) *Attorney, Agent, or Firm* — Banner & Witcoff, Ltd.

(57) ABSTRACT

Processes for converting methane and/or other hydrocarbons to synthesis gas (i.e., a gaseous mixture comprising $H_2$ and CO) are disclosed, in which at least a portion of the hydrocarbon(s) is reacted with $CO_2$. At least a second portion of the methane may be reacted with $H_2O$ (steam), thereby improving overall thermodynamics of the process, in terms of reducing endothermicity ($\Delta H$) and the required energy input, compared to "pure" dry reforming in which no $H_2O$ is present. Such dry reforming (reaction with $CO_2$ only) or $CO_2$-steam reforming (reaction with both $CO_2$ and steam) processes are advantageously integrated with Fischer-Tropsch synthesis to yield liquid hydrocarbon fuels. Further integration may involve the use of a downstream finishing stage involving hydroisomerization to remove FT wax. Yet other integration options involve the use of combined $CO_2$-steam reforming and FT synthesis stages (optionally with finishing) for producing liquid fuels from gas streams gen-
(Continued)

erated in a number of possible processes, including the hydropyrolysis of biomass.

34 Claims, 9 Drawing Sheets

Related U.S. Application Data division of application No. 15/813,814, filed on Nov. 15, 2017, now Pat. No. 10,738,247.

(51) Int. Cl.
| | | |
|---|---|---|
| B01D 3/14 | (2006.01) | |
| C07C 1/00 | (2006.01) | |
| C07C 1/04 | (2006.01) | |
| C07C 1/12 | (2006.01) | |
| C07C 5/13 | (2006.01) | |
| C07C 9/04 | (2006.01) | |
| C10G 47/32 | (2006.01) | |
| C10L 3/08 | (2006.01) | |
| C01B 32/50 | (2017.01) | |

(52) U.S. Cl.
CPC ............. *C07C 1/12* (2013.01); *C07C 5/13* (2013.01); *C07C 9/04* (2013.01); *C10G 47/32* (2013.01); *C10L 3/08* (2013.01); *C01B 32/50* (2017.08); *C10G 2300/1025* (2013.01); *C10G 2400/02* (2013.01); *C10G 2400/04* (2013.01); *C10G 2400/08* (2013.01); *C10G 2400/16* (2013.01)

(56) References Cited

U.S. PATENT DOCUMENTS

| | | | |
|---|---|---|---|
| 4,377,504 A | 3/1983 | Roberts et al. | |
| 4,594,468 A | 6/1986 | Minderhoud et al. | |
| 4,929,337 A | 5/1990 | Herbst et al. | |
| 5,336,655 A | 8/1994 | Basini et al. | |
| 5,468,368 A | 11/1995 | Baker, Jr. et al. | |
| 5,603,824 A | 2/1997 | Kyan et al. | |
| 5,741,440 A | 4/1998 | Cooper et al. | |
| 6,348,278 B1 | 2/2002 | LaPierre et al. | |
| 7,132,042 B2 | 11/2006 | Genetti et al. | |
| 7,166,268 B2 | 1/2007 | Fukunaga | |
| 7,241,401 B2 | 7/2007 | Aasberg-Petersen et al. | |
| 7,250,450 B2 | 7/2007 | Fenouil et al. | |
| 8,303,848 B2 | 11/2012 | Morita et al. | |
| 9,127,222 B2 | 9/2015 | Bhattacharya et al. | |
| 9,677,005 B1 | 6/2017 | Agee et al. | |
| 10,106,753 B1 | 10/2018 | Graham et al. | |
| 2002/0024038 A1 | 2/2002 | Iijima et al. | |
| 2002/0025987 A1 | 2/2002 | Iijima et al. | |
| 2004/0013917 A1 | 1/2004 | Ukai et al. | |
| 2006/0074132 A1 | 4/2006 | Allam et al. | |
| 2006/0182679 A1 | 8/2006 | Illinich et al. | |
| 2007/0172416 A1 | 7/2007 | Kawashima et al. | |
| 2008/0237542 A1 | 10/2008 | Schmidt et al. | |
| 2009/0035192 A1 | 2/2009 | Hwang | |
| 2009/0108238 A1 | 4/2009 | Wagner et al. | |
| 2009/0246118 A1 | 10/2009 | Drnevich et al. | |
| 2009/0294324 A1 | 12/2009 | Brandvold et al. | |
| 2009/0302275 A1 | 12/2009 | Chartier et al. | |
| 2010/0280288 A1 | 11/2010 | Joshi et al. | |
| 2010/0325957 A1 | 12/2010 | Klockow et al. | |
| 2011/0015282 A1 | 1/2011 | Yagi et al. | |
| 2011/0120009 A1 | 5/2011 | Klockow et al. | |
| 2011/0120010 A1 | 5/2011 | Tiwari et al. | |
| 2011/0309000 A1 | 12/2011 | Tanaka et al. | |
| 2012/0010304 A1 | 1/2012 | Tasaka | |
| 2012/0208905 A1 | 8/2012 | Sato et al. | |
| 2013/0305591 A1 | 11/2013 | McCall et al. | |
| 2013/0345326 A1 | 12/2013 | Bashir et al. | |
| 2014/0132028 A1 | 5/2014 | Yamada et al. | |
| 2014/0135409 A1 | 5/2014 | Aasberg-Petersen et al. | |
| 2014/0339475 A1 | 11/2014 | Moon et al. | |
| 2015/0104364 A1 | 4/2015 | Elomari | |
| 2015/0166913 A1 | 6/2015 | Brody et al. | |
| 2015/0218471 A1 | 8/2015 | Hannemann et al. | |
| 2016/0053187 A1* | 2/2016 | Hayasaka | G01N 24/085 208/141 |
| 2016/0121305 A1 | 5/2016 | Kartick et al. | |
| 2016/0145508 A1 | 5/2016 | Xu et al. | |
| 2016/0186071 A1 | 6/2016 | Moon et al. | |
| 2016/0222303 A1 | 8/2016 | Gao et al. | |
| 2016/0272895 A1 | 9/2016 | Wakamatsu et al. | |
| 2016/0311684 A1 | 10/2016 | Milanov et al. | |
| 2016/0362611 A1 | 12/2016 | Harris et al. | |
| 2017/0001176 A1 | 1/2017 | D'Souza et al. | |
| 2017/0158965 A1 | 6/2017 | Logue et al. | |
| 2017/0183583 A1 | 6/2017 | Ide et al. | |
| 2017/0274342 A1 | 9/2017 | Galloway et al. | |
| 2017/0283344 A1 | 10/2017 | Kuhn et al. | |
| 2018/0134967 A1 | 5/2018 | Ahmed et al. | |
| 2019/0233350 A1 | 8/2019 | Sankaranarayanan et al. | |
| 2021/0292666 A1 | 9/2021 | Greager et al. | |
| 2023/0119589 A1* | 4/2023 | Darcy | B01D 53/18 585/242 |
| 2023/0227743 A1* | 7/2023 | Foody | C10G 49/007 423/651 |
| 2023/0295523 A1* | 9/2023 | Foody | C12P 5/02 208/133 |
| 2023/0383194 A1* | 11/2023 | Agee | C10G 2/30 |
| 2024/0124786 A1* | 4/2024 | Alkilde | C10G 2/334 |

FOREIGN PATENT DOCUMENTS

| | | |
|---|---|---|
| CN | 106475096 A | 3/2017 |
| EA | 21624 B1 | 7/2015 |
| EP | 1852181 A1 | 11/2007 |
| EP | 1920830 A1 | 5/2008 |
| EP | 2308594 A2 | 4/2011 |
| EP | 2944606 A1 | 11/2015 |
| GB | 2247465 A | 3/1992 |
| JP | S6126693 A | 2/1986 |
| JP | H5208801 A | 8/1993 |
| JP | H0631321 A | 2/1994 |
| JP | H0789701 A | 4/1995 |
| JP | H08231204 A | 9/1996 |
| JP | H11130404 A | 5/1999 |
| JP | 2000104078 A | 4/2000 |
| JP | 2007016090 A | 1/2007 |
| JP | 2007238608 A | 9/2007 |
| JP | 4132295 B2 | 8/2008 |
| JP | 4934444 B2 | 8/2008 |
| JP | 2009242158 A | 10/2009 |
| JP | 2011127014 A | 6/2011 |
| JP | 2012107016 A | 6/2012 |
| JP | 2014511940 A | 5/2014 |
| JP | 2017007872 A | 1/2017 |
| KR | 20030061395 A | 7/2003 |
| RU | 2415904 | 5/2010 |
| RU | 2453366 C1 | 6/2012 |
| RU | 2577547 C2 | 3/2016 |
| WO | 2012069821 A1 | 5/2012 |
| WO | 2014014818 A1 | 1/2014 |
| WO | 2014132028 A1 | 9/2014 |
| WO | 2014195904 A1 | 12/2014 |
| WO | 2015099577 A1 | 7/2015 |
| WO | 2015/183200 A1 | 12/2015 |
| WO | 2016111411 A1 | 7/2016 |

OTHER PUBLICATIONS

Feb. 19, 2024—(EP) Extended European Search Report and Search Opinion—App EP23203968.5.
Mar. 6, 2024—(EP) Final Extended European Search Report and Search Opinion—App EP23196545.0.
Aug. 23, 2018—(WO) International Search Report—App PCT/US2017/061787.

(56) References Cited

OTHER PUBLICATIONS

Jan. 28, 2021—(WO) International Search Report—App PCT/2017/061787—Eng Trans.
Jan. 28, 2021—(RU) Office Action—App No. 2020119423—Eng Trans.
Lavoie, Jean-Michel, Review on dry reforming of methane, a potentially more environmentally-friendly approach to the increasing natural gas exploitation, Frontiers in Chemistry, v. 2, aet. 81, pp. 1-17, (2014).
Ozkara-Aydinoglu, Seyma, Thermodynamic equilibrium analysis of combined carbon dioxide reforming with steam reforming of methane to synthesis gas, International Journal of Hydrogen Energy 35, pp. 12821-12828, (2010).
Moskvichev, Yu A., 3 pages (2016) [concise statement of relevance under 37 CFR 1.98(a)(3)(i) and MPEP 609.04 (a)(III) in the English translation of the RU Office Action].

\* cited by examiner

PROCESSES AND SYSTEMS FOR REFORMING OF METHANE AND LIGHT HYDROCARBONS TO LIQUID HYDROCARBON FUELS

CROSS-REFERENCE TO RELATED APPLICATIONS

This application is a continuation of U.S. application Ser. No. 16/928,096, filed Jul. 14, 2020, now U.S. Pat. No. 11,667,853, which is a divisional of U.S. application Ser. No. 15/813,814, filed Nov. 15, 2017, now U.S. Pat. No. 10,738,247, which is hereby incorporated by reference in its entirety.

FIELD OF THE INVENTION

Aspects of the invention relate to reforming catalysts and processes for the reforming of methane and/or other hydrocarbons to produce a synthesis gas product comprising $H_2$ and CO, with further downstream conversion to liquid hydrocarbons.

DESCRIPTION OF RELATED ART

The ongoing search for alternatives to crude oil, for the production of hydrocarbon fuels is increasingly driven by a number of factors. These include diminishing petroleum reserves, higher anticipated energy demands, and heightened concerns over greenhouse gas (GHG) emissions from sources of non-renewable carbon. In view of its abundance in natural gas reserves, as well as in gas streams obtained from biological sources (biogas), methane has become the focus of a number of possible routes for providing liquid hydrocarbons. A key commercial process for converting methane into fuels involves a first conversion step to produce synthesis gas (syngas), followed by a second, downstream Fischer-Tropsch (FT) conversion step. In this second step, the synthesis gas containing a mixture of hydrogen ($H_2$) and carbon monoxide (CO) is subjected to successive cleavage of C—O bonds and formation of C—C bonds with the incorporation of hydrogen. This mechanism provides for the formation of hydrocarbons, and particularly straight-chain alkanes, with a distribution of molecular weights that can be controlled to some extent by varying the FT reaction conditions and catalyst properties. Such properties include pore size and other characteristics of the support material. The choice of catalyst can impact FT product yields in other respects. For example, iron-based FT catalysts tend to produce more oxygenates, whereas ruthenium as the active metal tends to produce exclusively paraffins.

With respect to the first conversion step, upstream of FT, known processes for the production of syngas from methane include partial oxidation reforming and autothermal reforming (ATR), based on the exothermic oxidation of methane with oxygen. Steam methane reforming (SMR), in contrast, uses steam as the oxidizing agent, such that the thermodynamics are significantly different, not only because the production of steam itself can require an energy investment, but also because reactions involving methane and water are endothermic. More recently, it has also been proposed to use carbon dioxide ($CO_2$) as the oxidizing agent for methane, such that the desired syngas is formed by the reaction of carbon in its most oxidized form with carbon in its most reduced form, according to:

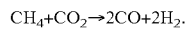

$$CH_4 + CO_2 \rightarrow 2CO + 2H_2.$$

This reaction has been termed the "dry reforming" of methane, and because it is highly endothermic, thermodynamics for the dry reforming of methane are less favorable compared to ATR or even SMR. However, the stoichiometric consumption of one mole of carbon dioxide per mole of methane has the potential to reduce the overall carbon footprint of liquid fuel production, providing a "greener" consumption of methane. This $CO_2$ consumption rate per mole of feed increases in the case of reforming higher hydrocarbons (e.g., $C_2$-$C_6$ paraffins), which may be desired, for example, if hydrogen production (e.g., for refinery processes) is the objective. In any event, the thermodynamic barrier nonetheless remains a major challenge and relates to the fact that $CO_2$ is completely oxidized and very stable, such that significant energy is needed for its activation as an oxidant. In view of this, a number of catalyst systems have been investigated for overcoming activation energy barrier for the dry reforming of methane, and these are summarized, for example, in a review by Lavoie (FRONTIERS IN CHEMISTRY (November 2014), Vol. 2 (81): 1-17), identifying heterogeneous catalyst systems as being the most popular in terms of catalytic approaches for carrying out this reaction.

Whereas nickel-based catalysts have shown effectiveness in terms of lowering the activation energy for the above dry reforming reaction, a high rate of carbon deposition (coking) of these catalysts has also been reported in Lavoie. The undesired conversion of methane to elemental carbon can proceed through methane cracking ($CH_4 \rightarrow C + 2H_2$) or the Boudouard reaction ($2CO \rightarrow C + CO_2$) at the reaction temperatures typically required for the dry reforming of methane. Therefore, although this reaction has been investigated as a promising route for syngas production, the commercialization of this technology, unlike other reforming technologies such as ATR and SMR, remains unrealized. This is due in large part to high rates of carbon formation and the accompanying deactivation of catalysts through coking, as encountered in the use of dry reforming catalyst systems that operate under conditions proposed to date. Finally, whereas other conventional reforming technologies have proven to be economically viable, these processes, and particularly SMR, are known to require significant upstream capital and operating expenses for the removal of sulfur and other poisons of the catalysts used. Otherwise, commercially acceptable periods of operation from a given catalyst loading cannot be achieved. Satisfactory solutions to these and other problems relating to the conventional reforming of hydrocarbons for the production of syngas and/or hydrogen have been sought but not achieved.

SUMMARY OF THE INVENTION

Aspects of the invention are associated with the discovery of reforming catalysts and processes for converting methane and/or other hydrocarbons to synthesis gas (i.e., a gaseous mixture comprising $H_2$ and CO) by reacting at least a portion of such hydrocarbon(s) with $CO_2$. Preferably, according to a $CO_2$-steam reforming reaction, at least a second portion of the hydrocarbon(s) (e.g., comprising the same hydrocarbon(s) as in the first portion) is reacted with $H_2O$ (steam), thereby improving overall thermodynamics of the process, in terms of reducing endothermicity ($\Delta H$) and the required energy input, compared to "pure" dry reforming in which no $H_2O$ is present. Representative reforming catalysts advantageously possess high activity and thereby can achieve significant levels of hydrocarbon (e.g., methane) conversion at temperatures below those used conventionally for dry reforming. These high activity levels, optionally in conjunction with using H₂O to provide at least a portion of the oxidant, contribute to an overall operating environment whereby coke formation is reduced and useful reforming catalyst life may be significantly extended.

Yet further important advantages reside in the sulfur tolerance of reforming catalysts described herein, whereby a pretreatment of a methane-containing feedstock (e.g., natural gas), or other hydrocarbon-containing feedstock, to reduce the concentration of H₂S and other sulfur-bearing contaminants is not required according to preferred embodiments, or is at least not as rigorous as in conventional reforming technologies. Also, to the extent that downstream sulfur removal may be desirable, such as prior to an FT synthesis step, this may be greatly simplified, considering that all or at least a substantial portion of sulfur-bearing contaminants other than 1-H₂S, such as mercaptans, can be oxidized in a dry reforming or CO₂-steam reforming reaction as described herein to SO₂, thereby rendering standard acid gas treatment (e.g., scrubbing) as a suitable and relatively simple option for such downstream sulfur removal.

Overall, improvements associated with the processes and reforming catalysts described herein are of commercial significance in terms of rendering dry reforming processes, or otherwise CO₂ and steam reforming (i.e., "CO₂-steam reforming") processes, as an economically viable alternative to conventional technologies such as autothermal reforming (ATR) and steam methane reforming (SMR). Moreover, the synthesis gas according to these processes may be produced with a favorable molar H₂:CO ratio (e.g., about 2:1) for downstream processing via the Fischer-Tropsch (FT) reaction, or at least with a molar ratio that may be readily adjusted to achieve such favorable values.

The demonstrated ability of CO₂-steam reforming processes described herein to produce synthesis gas products with favorable molar H₂:CO ratios, in a stable manner and with tolerance to sulfur-bearing contaminants that are often present in sources of methane (e.g., natural gas) and other light hydrocarbons, provides advantages in the use of these processes with additional steps for producing liquid hydrocarbons, for example gasoline- and diesel boiling-range hydrocarbon fractions. These advantages include greater simplicity of overall liquid hydrocarbon production processes, which may, for example, require fewer addition, separation, and/or recycle steps compared to conventional processes. This results not only in cost savings, but also in the possibility of providing such overall processes in an easily transportable (e.g., skid mounted) configuration, which may be brought to sources of natural gas, or other sources of components of gaseous mixtures as described herein, from which sources the transport of such components to conventional brick and mortar production facilities would otherwise be problematic. Advantages also include increased flexibility in terms of opportunities for integration with a wide variety of processes that generate CO₂— and/or light hydrocarbon-containing gas streams, including biomass conversion processes, fermentation processes, and industrial processes that generate CO₂-containing waste gases.

These and other embodiments, aspects, and advantages relating to the present invention are apparent from the following Detailed Description.

BRIEF DESCRIPTION OF THE DRAWINGS

A more complete understanding of the exemplary embodiments of the present invention and the advantages thereof may be acquired by referring to the following description in consideration of the accompanying figures, in which the same reference numbers are used to identify the same or similar features.

Figure 1A:
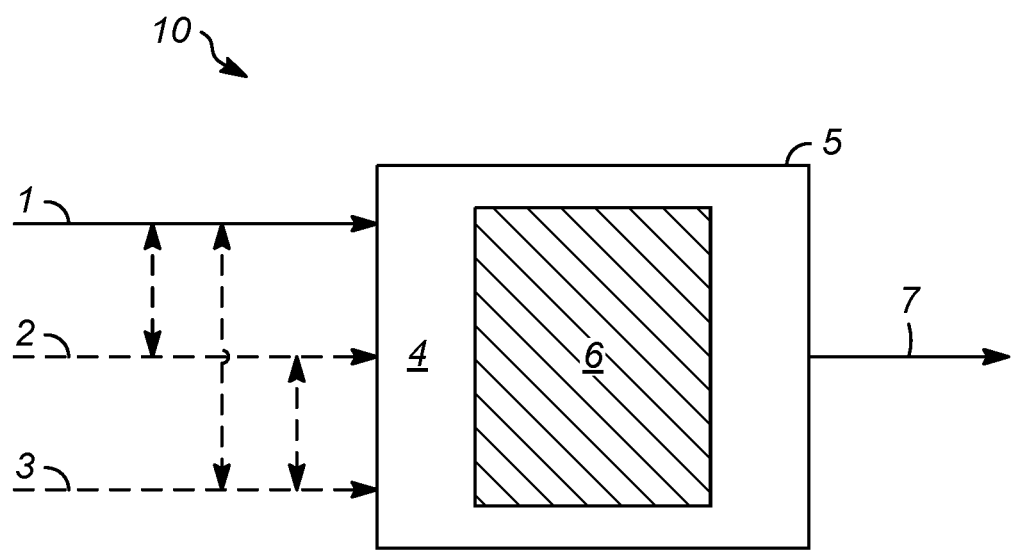
FIGS. 1A and 1B depict flowschemes that illustrate representative dry reforming and CO₂-steam reforming processes as described herein.

The figures should be understood to present illustrations of processes and certain associated results and parameters and/or principles involved. In order to facilitate explanation and understanding, FIGS. 1A, 1i, 3-7, 10, and 11 provide a simplified overview, with the understanding that these figures and elements shown are not necessarily drawn to scale. Valves, instrumentation, and other equipment and systems not essential to the understanding of the various aspects of the invention are not shown. As is readily apparent to one of skill in the art having knowledge of the present disclosure, processes for converting hydrocarbons such as methane, by dry reforming or CO₂-steam reforming, will have configurations and elements determined, in part, by their specific use.

DETAILED DESCRIPTION

The expressions "wt-%" and "mol-%," are used herein to designate weight percentages and molar percentages, respectively. The expressions "wt-ppm" and "mol-ppm" designate weight and molar parts per million, respectively.

For ideal gases, "mol-%" and "mol-ppm" are equal to percentages by volume and parts per million by volume, respectively.

As used herein, terms such as "$C_4^+$ hydrocarbons," "$C_{20}^+$ hydrocarbons," "$C_4$-$C_{19}$ hydrocarbons," etc. refer to hydrocarbons having greater than 4 carbon atoms, hydrocarbons having greater than 20 carbon atoms, hydrocarbons having from 4 to 19 carbon atoms, etc., respectively. Unless otherwise stated, these terms do not imply that hydrocarbons having all carbon numbers according to the specified ranges must necessarily be present. Unless otherwise stated, e.g., by the designation "normal $C_{20}^+$ hydrocarbons," hydrocarbons of all types are included in such terms (e.g., normal, branched, aromatic, naphthenic, olefinic, etc.).

The term "gaseous mixture" refers to the mixture comprising at least a hydrocarbon such as methane and also comprising $CO_2$ as an oxidant, which is subjected to dry reforming or $CO_2$-steam reforming (if water is also present in the gaseous mixture) by contact with a reforming catalyst as described herein. The term "gaseous mixture" refers generally to this mixture being completely or at least predominantly in the gas phase under conditions used for dry reforming or $CO_2$-steam reforming ("reforming conditions"), including the temperatures and pressures described herein as being suitable for these reactions. The term "gaseous mixture" does not preclude the presence of compounds in this mixture that, like water, are liquid under conditions of ambient temperature and pressure. Such compounds can include hydrocarbons found in liquid fuels including naphtha and jet fuels, for example $C_6$-$C_{16}$ hydrocarbons.

The terms "naphtha boiling-range hydrocarbons" and "gasoline boiling-range hydrocarbons" refer to a hydrocarbon fraction comprising hydrocarbons having boiling points within an initial ("front-end") distillation temperature of 35° C. (95° F.), characteristic of $C_5$ hydrocarbons, and an end point distillation temperature of 204° C. (399° F.). The term "jet fuel boiling-range hydrocarbons" refers to a hydrocarbon fraction comprising hydrocarbons having boiling points within a front-end distillation temperature of 204° C. (399° F.) and an end point distillation temperature of 271° C. (520° F.). The term "diesel boiling-range hydrocarbons" refers to a hydrocarbon fraction comprising hydrocarbons having boiling points within a front-end distillation temperature of 204° C. (399° F.) and an end point distillation temperature of 344° C. (651° F.). Accordingly, "diesel boiling-range hydrocarbons" encompass "jet fuel boiling-range hydrocarbons," but also include "heavy diesel boiling-range hydrocarbons" having boiling points within a front-end distillation temperature of 271° C. (520° F.) and an end point distillation temperature of 344° C. (651° F.). The term "VGO boiling-range hydrocarbons" refers to a hydrocarbon fraction comprising hydrocarbons having boiling points within a front-end distillation temperature of 344° C. (651° F.) and an end point distillation temperature of 538° C. (1000° F.). These front end and end point distillation temperatures of hydrocarbon fractions, such as naphtha boiling-range hydrocarbons, gasoline boiling-range hydrocarbons, jet fuel boiling-range hydrocarbons, and diesel boiling-range hydrocarbons, which are also characteristic of respective petroleum derived naphtha, gasoline, jet fuel, and diesel boiling-range fractions, are determined according to ASTM D86, with the end point being the 95% recovery value.

The term "substantially," as used in the phrase "substantially same" or "substantially the same," in reference to a given parameter, is meant to encompass values that deviate by less than 5% with respect to that parameter when measured in absolute terms (e.g., absolute temperature or absolute pressure). The term "substantially all" or "substantially all of" means "at least 95% of." The term "substantially complete" means "at least 95% complete."

Embodiments of the invention are directed to a process for producing a synthesis gas product (syngas), the process comprising contacting a gaseous mixture comprising (i) methane and/or other hydrocarbon(s) (e.g., any of $CH_4$, $C_2H_6$, $C_2H_4$, $C_3H_8$, $C_3H_6$, $C_4H_{10}$, $C_4H_8$, $C_5H_{12}$, $C_5H_{10}$, higher molecular weight hydrocarbons, and mixtures thereof) and (ii) $CO_2$, with a reforming catalyst comprising at least one (e.g., two, or more than two) noble metals on a solid support comprising cerium oxide. It is possible that $CO_2$ alone can serve as the oxidant for the methane and/or other hydrocarbon(s) to CO and $H_2$ according to the dry reforming of such hydrocarbons, which in the case of alkanes, for example, can be generalized as:

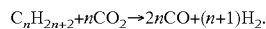
$$C_nH_{2n+2}+nCO_2 \rightarrow 2nCO+(n+1)H_2.$$

In preferred embodiments a combination of $CO_2$ and 1-120 can serve as the oxidant, that is, in embodiments in which the gaseous mixture further comprises $H_2O$. The reaction in this case is a "$CO_2$-steam reforming" reaction, which also includes steam reforming as a route for producing syngas from methane and/or other hydrocarbons, which in the case of alkanes, for example, can be generalized as:

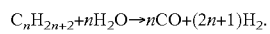
$$C_nH_{2n+2}+nH_2O \rightarrow nCO+(2n+1)H_2.$$

Whereas the theoretical molar $H_2$:CO ratio of a synthesis gas product formed from the dry reforming of methane is 1, the addition of steam reforming, in the $CO_2$-steam reforming of methane, advantageously provides the potential to increase this molar ratio to values more favorable for downstream Fischer-Tropsch synthesis to produce liquid hydrocarbons, according to the reaction:

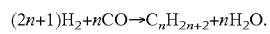
$$(2n+1)H_2+nCO \rightarrow C_nH_{2n+2}+nH_2O.$$

From this, it can be observed that $C_4^+$ hydrocarbons, such as $C_4$-$C_{12}$ hydrocarbons, which are desirable as fuels or components of fuels, are formed ideally at molar $H_2$:CO ratios approaching 2. Importantly, the use of steam ($H_2O$) as an oxidant in combination with $CO_2$ provides an advantageous "handle" or control parameter for adjusting the molar $H_2$:CO ratio of the synthesis gas product over a wide range of $CO_2$-steam reforming conditions. In fact, for any given set of such conditions (e.g., conditions within the $CO_2$-steam reforming reactor such as temperature, pressure, weight hourly space velocity, and reforming catalyst formulation) under which the combined $CO_2$ and steam reforming reactions are carried out, a relationship can be established between the molar $H_2O$:$CO_2$ ratio of the gaseous mixture (e.g., combined $CO_2$-steam reforming reactor feed) and the molar $H_2$:CO ratio of the synthesis gas product (e.g., $CO_2$-steam reforming reactor effluent). Whereas the dry reforming and steam reforming of hydrocarbons other than methane produce $H_2$ and CO at other molar ratios, directionally the same shifts or adjustments in product yields may be achieved by varying the relative amounts of the oxidants $H_2O$ and $CO_2$ in the gaseous mixture that is subjected to $CO_2$-steam reforming. Accordingly, embodiments of the invention are directed to a $CO_2$-steam reforming process comprising determining a molar $H_2$:CO ratio of the synthesis gas product and, based on the molar $H_2$:CO ratio, adjusting a molar $H_2O$:$CO_2$ ratio of the gaseous mixture toward a target molar $H_2$:CO ratio of the synthesis gas product, for example a target molar $H_2$:CO ratio of 2:1, or otherwise a target molar $H_2$:CO ratio range generally from about 1.5:1 to about 2.5:1, typically from about 1.5:1 to about 2.3:1, and often from about 1.8:1 to about 2.2:1.

More specifically, the molar $H_2O:CO_2$ ratio of the gaseous mixture may be increased to increase, toward the target molar $H_2:CO$ ratio, an observed molar $H_2:CO$ ratio of the synthesis gas product that is below the target. Conversely, the molar $H_2O:CO_2$ ratio of the gaseous mixture may be decreased to decrease, toward the target molar $H_2:CO$ ratio, an observed molar $H_2:CO$ ratio of the synthesis gas product that is above the target. Any such adjustments to the molar $H_2O:CO_2$ ratio of the gaseous mixture may be performed, for example, by adjusting the flow rate(s) of one or more components of the gaseous mixture (e.g., combined feed), such as one or more of a methane-containing feedstock (or hydrocarbon-containing feedstock generally), a $CO_2$-containing oxidant, and an $H_2O$-containing oxidant, relative to the flow rate(s) of one or more other of such components. According to a specific example, the molar $H_2O:CO_2$ ratio of the combined feed to the $CO_2$-steam reforming reactor may be increased or decreased, by increasing or decreasing, respectively, the flow rate of steam (as the $H_2O$-containing oxidant), thereby resulting in a respective increase or decrease in the molar $H_2O:CO_2$ ratio of the gaseous mixture.

In addition to providing the ability to control the molar $H_2:CO$ ratio of the synthesis gas product over a favorable range of values, the use of steam ($H_2O$) as an oxidant in combination with $CO_2$ furthermore surprisingly reduces the rate of carbon (coke) formation compared to pure dry reforming, thereby extending the life of catalysts as described herein. Accordingly, further embodiments of the invention are directed to a $CO_2$-steam reforming process in which the rate of carbon formation (e.g., using suitable ratios or concentrations/partial pressures of $CO_2$ and $H_2O$ oxidants, in combination with a reforming catalyst as described herein) is less than the rate of carbon formation of a baseline process (i.e., baseline dry reforming process), in which all parameters are maintained the same, except for the replacement of $H_2O$ in the gaseous mixture (e.g., combined $CO_2$-steam reforming reactor feed) with an equimolar amount of oxygen as $CO_2$ (i.e., replacement of the moles of $H_2O$ with ½ the moles of $CO_2$). Coupled with this comparatively lower carbon formation relative to the baseline process, the synthesis gas product may have a molar $H_2/CO$ ratio as described herein (e.g., from about 1.5:1 to about 2.3:1).

$CO_2$-steam reforming, as described herein, can be performed to produce a synthesis gas product having a favorable molar $H_2:CO$ ratio in the ranges described above, such as from about 1.5:1 to about 2.5:1, from about 1.5:1 to about 2.3:1, and from about 1.8:1 to about 2.2:1. Such ranges, encompassing 2:1, are particularly advantageous in the case of downstream processing of the synthesis gas product in an FT synthesis stage, as described herein, to produce liquid hydrocarbons. In particular, a step of converting $H_2$ and CO in the synthesis gas product to hydrocarbons, including $C_4^+$ hydrocarbons (including hydrocarbons that are liquid at ambient temperature and pressure) that are provided in an FT product, may be carried out with an FT feed having a substantially same $H_2:CO$ molar ratio as in the synthesis gas product, produced by the upstream $CO_2$-steam reforming. That is, the FT feed may be obtained preferably without adjustment of the $H_2:CO$ molar ratio of the synthesis gas product, such as by adding or removing $H_2$ and/or CO or otherwise converting or producing these components (e.g., without adding $H_2$ to increase this molar ratio and/or without the use of a separate water-gas shift reaction or reverse water-gas shift reaction). According to some embodiments, the FT feed may be obtained at substantially the same $H_2:CO$ molar ratio as in the synthesis gas product, by condensing water from this product, prior to converting $H_2$ and CO to hydrocarbons in the FT synthesis stage.

According to some embodiments, the FT feed may be obtained without any change in composition of the synthesis gas product. For example, some or all of the synthesis gas product may be used directly in the FT synthesis stage without any intervening operation that would impact its composition (e.g., by the addition, removal, or conversion of components that would alter this composition).

The above ranges of molar $H_2:CO$ ratios of the synthesis gas product, encompassing 2:1, are likewise advantageous in the case of downstream processing of the synthesis gas product in a methanol production stage to produce methanol according to the reaction $2H_2+CO \rightarrow CH_3OH$. In particular, a step of converting $H_2$ and CO in the synthesis gas product to methanol that is provided in a methanol product, may be carried out with a methanol synthesis feed having a substantially same $H_2:CO$ molar ratio as in the synthesis gas product, produced by the upstream $CO_2$-steam reforming. That is, the methanol synthesis feed may be obtained preferably without adjustment of the $H_2:CO$ molar ratio of the synthesis gas product, such as by adding or removing $H_2$ and/or CO or otherwise converting or producing these components (e.g., without adding $H_2$ to increase this molar ratio and/or without the use of a separate water-gas shift reaction or reverse water-gas shift reaction). According to some embodiments, the methanol synthesis feed may be obtained at substantially the same $H_2:CO$ molar ratio as in the synthesis gas product, by condensing water from this product. According to some embodiments, the methanol synthesis feed may be obtained without any change in composition of the synthesis gas product. For example, some or all of the synthesis gas product may be used directly in the methanol production stage without any intervening operation that would impact its composition (e.g., by the addition, removal, or conversion of components that would alter this composition). Methanol production from the synthesis gas product may be carried out at a temperature from about 204° C. (400° F.) to about 316° C. (600° F.) and a pressure from about 4.5 MPa (650 psig) to about 11.7 MPa (1700 psig). Methanol synthesis catalysts typically comprise Cu and ZnO, supported on a metal oxide such as alumina ($Al_2O_3$).

In the case of production of methanol from the synthesis gas product, this methanol may be further reacted in a dehydration stage to produce dimethyl ether (DME) according to the reaction $2CH_3OH \rightarrow CH_3OCH_3+H_2O$. Catalysts and conditions for conducting this reaction stage are described, for example, in U.S. Pat. No. 5,037,511; US 2004/0034255; and U.S. Pat. No. 8,451,630. Alternatively, DME may be produced directly from the synthesis gas product in a direct DME production stage, without an intervening methanol production stage. In this regard, dry reforming, as described herein, can be performed to produce a synthesis gas product having a favorable molar $H_2:CO$ ratio in ranges encompassing 1:1 that are suitable for carrying out the reaction $3H_2+3CO \rightarrow CH_3O\ CH_3+CO_2$, as described, for example, in Takeishi et al. (Recent Advances in Energy & Environment). Suitable molar $H_2:CO$ ratios are from about 0.5:1 to about 1.5:1, from about 0.5:1 to about 1.3:1, or from about 0.8:1 to about 1.2:1. In particular, a step of converting $H_2$ and CO in the synthesis gas product to DME that is provided in a DME product, may be carried out with a DME synthesis feed having a substantially same $H_2:CO$ molar ratio as in the synthesis gas product, produced by the upstream dry reforming. That is, the DME synthesis feed may be obtained preferably without adjustment of the molar $H_2$:CO ratio of the synthesis gas product, such as by adding or removing $H_2$ and/or CO or otherwise converting or producing these components (e.g., without adding $H_2$ to increase this molar ratio and/or without the use of a separate water-gas shift reaction or reverse water-gas shift reaction). According to some embodiments, the DME synthesis feed may be obtained at substantially the same molar $H_2$:CO ratio as in the synthesis gas product, by condensing water from this product. According to some embodiments, the DME synthesis feed may be obtained without any change in composition of the synthesis gas product. For example, some or all of the synthesis gas product may be used directly in the direct DME production stage, without any intervening operation that would impact its composition (e.g., by the addition, removal, or conversion of components that would alter this composition).

In addition to producing a synthesis gas product having a desirable molar $H_2$:CO ratio that can be tailored to particular, downstream reaction steps as described above, reforming catalysts as described herein furthermore exhibit a surprising degree of sulfur tolerance, which is particularly advantageous, for example, in the case of methane-containing feedstocks comprising or derived from natural gas that, depending on its source, may contain a significant concentration (e.g., several weight percent by volume or more) of $H_2S$. In this regard, conventional steam methane reforming (SMR) processes require pretreatment to reduce the feed total sulfur content to typically less than 1 mol-ppm to protect the reforming catalyst from sulfur poisoning. In contrast, according to representative embodiments of the present invention, the gaseous mixture or any of its components, particularly the hydrocarbon-containing feedstock, is not subjected to, or otherwise has not undergone, a sulfur removal pretreatment step. Such embodiments provide substantial economic benefits over known processes with stringent desulfurization requirements and associated expenses, as necessary to achieve favorable reforming catalyst life. In contrast to such known processes, a gaseous mixture in a dry reforming or $CO_2$-steam reforming process as described herein may comprise sulfur generally at any concentration representative of the source of the hydrocarbon feedstock, such as natural gas, not having undergone pretreatment for sulfur removal, but also accounting for the potential dilution of the sulfur when combined with other components of the gaseous mixture (e.g., $CO_2$) having a lower sulfur concentration. For example, the gaseous mixture may comprise generally at least about 1 mole-ppm (e.g., from about 1 mol-ppm to about 10 mol-%) total sulfur (e.g., as $H_2S$ and/or other sulfur-bearing contaminants). The gaseous mixture may comprise typically at least about 10 mol-ppm (e.g., from about 10 mol-ppm to about 1 mol-%) and often at least about 100 mol-ppm (e.g., from about 100 mol-ppm to about 1000 mol-ppm) of total sulfur. For example, a range from about 500 mol-ppm to about 1000 mol-ppm of total sulfur, according to particular embodiments, generally poses no, or at least a negligible, adverse effect on the stability of reforming catalysts as described herein.

With respect to sulfur tolerance of reforming catalysts described herein, further aspects of the invention are associated with the discovery that higher levels (concentrations) of sulfur in the gaseous mixture may be compensated for by increasing the reaction temperature, i.e., temperature of the bed of reforming catalyst as described herein, contained in a reforming reactor (which may be either a dry reforming reactor or a $CO_2$-steam reforming reactor, with the latter term being applicable to the gaseous mixture within the reactor comprising both $CO_2$ and $H_2O$). That is, increased sulfur concentrations have been found to impact reforming catalyst activity, as measured by decreased conversion of methane and/or or other hydrocarbon(s) in the gaseous mixture, if all other operating parameters remain unchanged. However, the desired conversion level can be restored by increasing the reaction temperature. For example, under certain operating conditions, a 28° C. (50° F.) increase can be sufficient to restore a loss in reforming catalyst activity that accompanies a concentration of 800 mol-ppm $H_2S$ in the gaseous mixture, relative to the activity without any sulfur in the gaseous mixture. Accordingly, embodiments of the invention are directed to a dry reforming process or a $CO_2$-steam reforming process as described herein comprising determining a conversion of methane and/or other hydrocarbon(s) (e.g., a conversion of combined $C_1$-$C_4$ hydrocarbons or combined $C_1$-$C_3$ hydrocarbons), or otherwise determining a sulfur level (such as an $H_2S$ level) in the gaseous mixture or synthesis gas product and, based on the conversion or sulfur level, adjusting the reaction temperature toward a target conversion of methane and/or other hydrocarbon(s), for example a target conversion of at least about 75% (e.g., any specific conversion value in the range from about 75% to about 100%), such as a target conversion of at least about 85% (e.g., any specific conversion value in the range from about 85% to about 99%).

Importantly, however, such decreases in the activity of reforming catalysts described herein, accompanying increases in the concentration of sulfur in the gaseous mixture, are not further accompanied by any appreciable loss in reforming catalyst stability. That is, the compensating reforming reactor temperature increases, as described herein to offset higher sulfur levels, do not significantly impact the ability of the reforming catalyst to achieve stable operating performance with respect to dry reforming or $CO_2$-steam reforming over an extended period. This finding is contrary to expectations based on conventional reforming technologies, in which the presence of even small quantities (e.g., mol-ppm levels) of sulfur in feeds must be prevented to avoid deactivation and costly premature replacement of the catalyst. A characteristic sulfur tolerance, or activity stability in the presence of sulfur-bearing contaminants, of reforming catalysts as described herein can be determined according to a standard test in which a small, 5-100 gram catalyst sample is loaded into a fixed-bed reforming reactor and contacted with a feed blend of 30 mol-% methane, 30 mol-% $CO_2$, and 30 mol-% $H_2O$ that is spiked with 800 mol-ppm of $H_2S$. In this standard test, with flowing conditions of 0.7 hr$^{-1}$ WHSV, a catalyst bed temperature of 788° C. (1450° F.), and a $CO_2$-steam reforming reactor pressure of 138 kPa (20 psig), a conversion of the methane of at least 85%, and preferably at least 95%, is maintained, at constant catalyst bed temperature, for at least 50 hours of operation, and more typically for at least 100 hours of operation, or even for at least 400 hours of operation.

The tolerance, or "robustness" of reforming catalysts described herein is further manifested in a high stability against deactivation in the presence of other compounds in the gaseous mixture, including higher molecular weight hydrocarbons such as reactive aromatic hydrocarbons and/or olefinic hydrocarbons that are normally considered prone to causing reforming catalyst deactivation through coking. For example, the gaseous mixture may comprise aromatic and olefinic hydrocarbons in a combined amount of generally at least about 1 mole-% (e.g., from about 1 mol-% to about 25 mol-%), such as at least about 3 mol-% (e.g., from about 3 mol-% to about 20 mol-%) or more particularly at least about 5 mol-% (e.g., from about 5 mol-% to about 15 mol-%). At such levels of aromatic and/or olefinic hydrocarbons, reforming catalyst stability may be exhibited according to the same activity stability test as defined above with respect to sulfur tolerance, with the exception of the feed blend containing these concentrations of aromatic and/or olefinic hydrocarbons as opposed to $H_2S$. This tolerance of reforming catalysts as described herein with respect to both sulfur and reactive hydrocarbons allows for the reforming of wide-ranging hydrocarbon-containing feedstocks, including various fractions (e.g., naphtha and jet fuel) obtained from crude oil refining as described in greater detail below.

More generally, the gaseous mixture, and particularly the hydrocarbon-containing feedstock component of this mixture, may comprise, in addition to methane, other hydrocarbons such as $C_2$, $C_3$, and/or $C_4$ hydrocarbons (e.g., ethane, propane, propylene, butane, and/or butenes) that may be present in natural gas and/or other sources of methane). Alternatively, reforming catalysts as described herein may be used for dry reforming or $CO_2$-steam reforming of predominantly, or only, higher molecular weight hydrocarbons, such as in the case of the hydrocarbons in gaseous mixture comprising, or optionally consisting of, any one or more compounds selected from the group consisting of a $C_4$ hydrocarbon, a $C_5$ hydrocarbon, a $C_6$ hydrocarbon, a $C_7$ hydrocarbon, a $C_8$ hydrocarbon, a $C_9$ hydrocarbon, a $C_{10}$ hydrocarbon, a $C_{11}$ hydrocarbon, a $C_{12}$ hydrocarbon, a $C_{13}$ hydrocarbon, a $C_{14}$ hydrocarbon, a $C_{15}$ hydrocarbon, a $C_{16}$ hydrocarbon, a $C_{17}$ hydrocarbon, a Cis hydrocarbon, and combinations thereof. For example, the hydrocarbons in the gaseous mixture may comprise, or consist of, $C_4$-$C_8$ or $C_4$-$C_6$ hydrocarbons, in the case of dry reforming or $CO_2$-steam reforming of naphtha boiling-range hydrocarbons (naphtha reforming). As another example, the hydrocarbons in the gaseous mixture may comprise, or consist of, $C_8$-$C_{18}$ or $C_5$-$C_{14}$ hydrocarbons, in the case of dry reforming or $CO_2$-steam reforming of jet fuel boiling-range hydrocarbons (jet fuel reforming). Such naphtha boiling-range hydrocarbons and jet fuel boiling-range fractions are normally obtained as products from crude oil refining and, as such, can be a source of sulfur-bearing contaminants in the gaseous mixture. In representative embodiments, the gaseous mixture may comprise methane and/or any of the hydrocarbons described herein in a combined amount generally from about 5 mol-% to about 85 mol-%, typically from about 10 mol-% to about 65 mol-%, and often from about 20 mol-% to about 45 mol-%. The gaseous mixture may further comprise $CO_2$ in an amount generally from about 8 mol-% to about 90 mol %, typically from about 15 mol-% to about 75 mol-%, and often from about 20 mol-% to about 50 mol-%. In the case of $CO_2$-steam reforming, the gaseous mixture may comprise $H_2O$ in an amount generally from about 15 mol-% to about 70 mol-%, typically from about 20 mol-% to about 60 mol-%, and often from about 25 mol-% to about 55 mol-%. The balance of the gaseous mixture may include contaminants such as $H_2S$ and/or other sulfur-bearing contaminants as described above.

In the case of gaseous mixtures comprising methane and/or light hydrocarbons (e.g., $C_2$-$C_3$ or $C_2$-$C_4$ hydrocarbons), the synthesis gas product of dry reforming or $CO_2$-steam reforming may advantageously be used with a favorable molar $H_2$:CO ratio in the downstream production of liquid hydrocarbon fuels through Fischer-Tropsch synthesis, as described above. The synthesis gas may alternatively be used for other downstream applications associated with conventional steam methane reforming (SMR). For example, Tarun (INTERNATIONAL JOURNAL OF GREENHOUSE GAS CONTROL I (2007): 55-61) describes a conventional hydrogen production process involving SMR. If dry reforming or $CO_2$-steam reforming, as described herein, is applied in hydrogen production, according to embodiments of the invention, representative processes may further comprise steps of (i) subjecting the synthesis gas product to one or more water-gas shift (WGS) reaction stages to increase its hydrogen content and/or (ii) separating the effluent of the WGS stage(s), or otherwise separating the synthesis gas product without intervening WGS stage(s), as the case may be (e.g., by pressure-swing adsorption (PSA) or membrane separation), to provide a hydrogen-enriched product stream and a hydrogen-depleted PSA tail gas stream (or simply "PSA tail gas"). The hydrogen-enriched product stream may then be used in a conventional refinery process such as a hydrotreating process (e.g., hydrodesulfurization, hydrocracking, hydroisomerization, etc.). The hydrogen-depleted PSA tail gas stream may then be separated to recover hydrogen and/or used as combustion fuel to satisfy at least some of the heating requirements of the dry reforming or $CO_2$-steam reforming. In yet further embodiments, the CO— and $H_2$-containing PSA tail gas may be passed to a biological fermentation stage for the production of fermentation products such as alcohols (e.g., ethanol).

The gaseous effluent from the fermentation stage may then be separated to recover hydrogen and/or used as combustion fuel as described above. With respect to conventional hydrogen production, the further integration of a biological fermentation stage is described, for example, in U.S. Pat. Nos. 9,605,286; 9,145,300; US 2013/0210096; and US 2014/0028598. As an alternative to integration in a hydrogen production process, dry reforming or $CO_2$-steam reforming as described herein may be used to provide a synthesis gas product that is used directly in the downstream production of fermentation products using suitable carboxydotrophic bacteria (e.g., of the species Clostridium autoethanogenum or Clostridium ljungdahlii). In either case, i.e., with or without such integration, the microorganisms used for the fermentation may be sulfur tolerant or even require sulfur in the cell culture medium, such that the sulfur tolerance of reforming catalysts as described herein can be particularly advantageous over conventional reforming catalysts, in terms of compatibility and cost savings associated with the elimination of, or at the least reduced requirements for, upstream sulfur removal.

Aspects of the invention therefore relate to dry reforming processes and $CO_2$-steam reforming processes for producing a synthesis gas product (i.e., comprising both $H_2$ and CO, and optionally other gases such as unconverted $CO_2$, $H_2O$, and/or hydrocarbons). In representative embodiments, a gaseous mixture comprising methane and/or other hydrocarbon(s) may be provided batchwise, but preferably as a continuous flow, to a reactor of a dry reforming process (i.e., a dry reforming reactor, in the case of the feed or gaseous mixture further comprising $CO_2$ but no water) or a $CO_2$-steam reforming process (i.e., a $CO_2$-steam reforming reactor, in the case of the feed or gaseous mixture further comprising both $CO_2$ and water), with the general term "reforming reactor" encompassing either case. A synthesis gas product, in turn, may be withdrawn batchwise (if the gaseous mixture is provided batchwise), but preferably as a continuous flow (if the gaseous mixture is provided as a continuous flow), from the dry reforming reactor or the $CO_2$-steam reforming reactor, as the case may be.

In addition to $H_2$, CO, and optionally other gases, water ($H_2O$) may also be present in the synthesis gas product, although at least a portion of the water that is present in vapor form may be readily separated by cooling/condensation, for example upstream of a Fischer-Tropsch synthesis reactor (FT reactor) used to convert the synthesis gas product to liquid hydrocarbons. Neither water nor $CO_2$ in the synthesis gas product has an effect on its molar $H_2$:CO ratio which, as described above, is an important parameter in determining the suitability of the synthesis gas product as a direct feed stream to the FT reactor.

In representative processes, a gaseous mixture comprising methane and/or other light hydrocarbon(s) (e.g., ethane, ethylene, propane, and/or propylene) and $CO_2$, as well as optionally $H_2O$, is contacted with a reforming catalyst having activity for carrying out the reforming of such hydrocarbon(s). In particular, such hydrocarbon(s), for example the majority of such hydrocarbons, may be reformed (i) through their oxidation with some or all of the $CO_2$ only, according to a dry reforming process, or (ii) through their oxidation with both some or all of the $CO_2$ and some of all of the $H_2O$ (if present), according to a $CO_2$-steam reforming process.

As described above, aspects of the invention are associated with the discovery of reforming catalysts for such dry reforming and $CO_2$-steam reforming processes, exhibiting important advantages, particularly in terms of sulfur tolerance and/or a reduced rate of carbon formation (coking), compared to conventional reforming catalysts. These characteristics, in turn, reduce the rate of catalyst deactivation through poisoning and/or coking mechanisms that chemically and/or physically block active catalyst sites. Further improvements in reforming catalyst stability result at least in part from the high activity of reforming catalysts described herein, as necessary to lower the substantial activation energy barrier associated with the use of $CO_2$ as an oxidant for methane and/or other hydrocarbon(s), as described above. This high activity manifests in lower operating (dry reforming reactor or $CO_2$-steam reforming reactor or dry reforming catalyst bed or $CO_2$-steam reforming catalyst bed) temperatures, which further contribute to the reduced rate of carbon deposition (coke formation) on the reforming catalyst surface and extended, stable operation. According to particular embodiments, processes utilizing reforming catalysts described herein can maintain stable operating parameters as described herein, for example in terms of hydrocarbon conversion (e.g., at least about 85% conversion of methane and/or other hydrocarbon(s)) and/or molar $H_2$/CO ratio (e.g., from about 1.5:1 to about 2.3:1) of the synthesis gas product, for at least about 100, at least about 300, or even at least about 500, hours of continuous or possibly discontinuous operation. This may be an operating period over which (i) the reforming catalyst does not undergo regeneration, for example according to a reforming process utilizing the catalyst as a fixed bed within the reforming reactor and/or (ii) the temperature of the reforming reactor or respective dry reforming catalyst bed or $CO_2$-steam reforming catalyst bed is not raised beyond a threshold temperature difference from the start of the time period to the end of the time period, with this threshold temperature difference being, for example, 100° C. (180° F.), 50° C. (90° F.), 25° C. (45° F.), 10° C. (18° F.), or even 5° C. (9° F.).

Representative reforming catalysts suitable for catalyzing the reaction of methane and/or other hydrocarbon(s) with $CO_2$ and optionally also with $H_2O$ comprise a noble metal, and possibly two or more noble metals, on a solid support. The solid support preferably comprises a metal oxide, with cerium oxide being of particular interest. Cerium oxide may be present in an amount of at least about 80 wt-% and preferably at least about 90 wt-%, based on the weight of the solid support (e.g., relative to the total amount(s) of metal oxide(s) in the solid support). The solid support may comprise all or substantially all (e.g., greater than about 95 wt-%) cerium oxide. Other metal oxides, such as aluminum oxide, silicon oxide, titanium oxide, zirconium oxide, magnesium oxide, strontium oxide, etc., may also be present in the solid support, in combined amounts representing a minor portion, such as less than about 50 wt-%, less than about 30 wt-%, or less than about 10 wt-%, of the solid support. In other embodiments, the solid support may comprise such other metal oxides alone or in combination, with a minor portion (e.g., less than about 50 wt-% or less than about 30 wt-%) of cerium oxide.

Noble metals are understood as referring to a class of metallic elements that are resistant to oxidation. In representative embodiments, the noble metal, for example at least two noble metals, of the reforming catalyst may be selected from the group consisting of platinum (Pt), rhodium (Rh), ruthenium (Ru), palladium (Pd), silver (Ag), osmium (Os), iridium (Ir), and gold (Au), with the term "consisting of" being used merely to denote group members, according to a specific embodiment, from which the noble metal(s) are selected, but not to preclude the addition of other noble metals and/or other metals generally. Accordingly, a reforming catalyst comprising a noble metal embraces a catalyst comprising at least two noble metals, as well as a catalyst comprising at least three noble metals, and likewise a catalyst comprising two noble metals and a third, non-noble metal such as a promoter metal (e.g., a transition metal). According to preferred embodiments, the noble metal is present in an amount, or alternatively the at least two noble metals are each independently present in amounts, from about 0.05 wt-% to about 5 wt-%, from about 0.3 wt-% to about 3 wt-%, or from about 0.5 wt-% to about 2 wt-%, based on the weight of the catalyst. For example, a representative reforming catalyst may comprise the two noble metals Pt and Rh, and the Pt and Rh may independently be present in an amount within any of these ranges (e.g., from about 0.05 wt-% to about 5 wt-%). That is, either the Pt may be present in such an amount, the Rh may be present in such an amount, or both Pt and Rh may be present in such amounts.

In representative embodiments, the at least two noble metals (e.g., Pt and Rh) may be substantially the only noble metals present in the reforming catalyst, such that, for example, any other noble metal(s) is/are present in an amount or a combined amount of less than about 0.1 wt-%, or less than about 0.05 wt-%, based on the weight of the reforming catalyst. In further representative embodiments, that at least two noble metals (e.g., Pt and Rh) are substantially the only metals present in the reforming catalyst, with the exception of metals present in the solid support (e.g., such as cerium being present in the solid support as cerium oxide). For example, any other metal(s), besides at least two noble metals and metals of the solid support, may be present in an amount or a combined amount of less than about 0.1 wt-%, or less than about 0.05 wt-%, based on the weight of the reforming catalyst. Any metals present in the catalyst, including noble metal(s), may have a metal particle size in the range generally from about 0.3 nanometers (nm) to about 20 nm, typically from about 0.5 nm to about 10 nm, and often from about 1 nm to about 5 nm.

The noble metal(s) may be incorporated in the solid support according to known techniques for catalyst preparation, including sublimation, impregnation, or dry mixing. In the case of impregnation, which is a preferred technique, an impregnation solution of a soluble compound of one or more of the noble metals in a polar (aqueous) or non-polar (e.g., organic) solvent may be contacted with the solid support, preferably under an inert atmosphere. For example, this contacting may be carried out, preferably with stirring, in a surrounding atmosphere of nitrogen, argon, and/or helium, or otherwise in a non-inert atmosphere, such as air. The solvent may then be evaporated from the solid support, for example using heating, flowing gas, and/or vacuum conditions, leaving the dried, noble metal-impregnated support. The noble metal(s) may be impregnated in the solid support, such as in the case of two noble metals being impregnated simultaneously with both being dissolved in the same impregnation solution, or otherwise being impregnated separately using different impregnation solutions and contacting steps. In any event, the noble metal-impregnated support may be subjected to further preparation steps, such as washing with the solvent to remove excess noble metal(s) and impurities, further drying, calcination, etc. to provide the reforming catalyst.

The solid support itself may be prepared according to known methods, such as extrusion to form cylindrical particles (extrudates) or oil dropping or spray drying to form spherical particles. Regardless of the specific shape of the solid support and resulting catalyst particles, the amounts of noble metal(s) being present in the reforming catalyst, as described above, refer to the weight of such noble metal(s), on average, in a given catalyst particle (e.g., of any shape such as cylindrical or spherical), independent of the particular distribution of the noble metals within the particle. In this regard, it can be appreciated that different preparation methods can provide different distributions, such as deposition of the noble metal(s) primarily on or near the surface of the solid support or uniform distribution of the noble metal(s) throughout the solid support. In general, weight percentages described herein, being based on the weight of the solid support or otherwise based on the weight of reforming catalyst, can refer to weight percentages in a single catalyst particle but more typically refer to average weight percentages over a large number of catalyst particles, such as the number in a reforming reactor that form a catalyst bed as used in processes described herein.

Figure 1B:
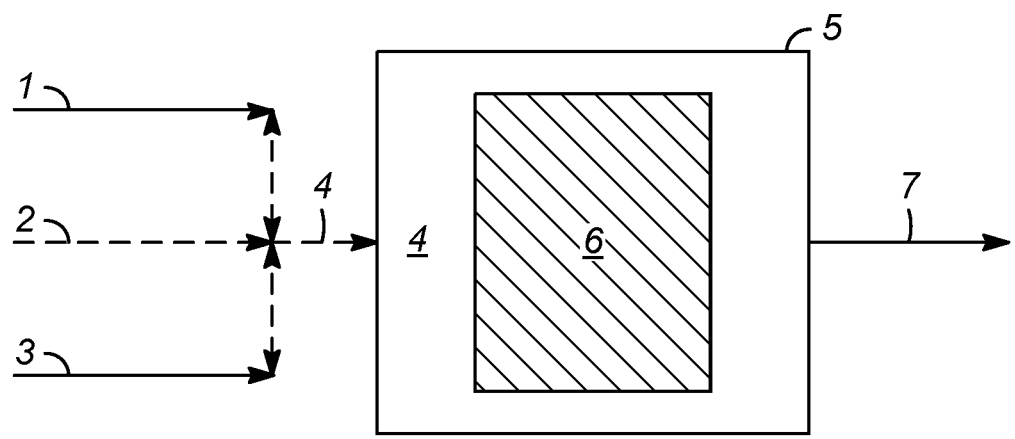

Simplified illustrations of dry reforming processes and optionally $CO_2$-steam reforming processes 10 are depicted in FIGS. 1A and 1B. In either of these embodiments, gaseous mixture 4 comprising one or more hydrocarbons (e.g., methane) and $CO_2$, may reside within reforming reactor 5 in the form of a vessel that is used to contain a bed of reforming catalyst 6, as described above, under reforming conditions at which gaseous mixture 4 and reforming catalyst 6 are contacted. According to the embodiment illustrated in FIG. 1A, gaseous mixture 4 may be provided within reforming reactor 5 from hydrocarbon-containing feedstock 1 alone. For example, a representative hydrocarbon-containing feedstock is a methane-containing feedstock that is obtained from biomass gasification or pyrolysis, including hydrogasification or hydropyrolysis, and may further comprise $CO_2$ and $H_2O$. Such a hydrocarbon-containing feedstock may thereby itself provide gaseous mixture 4 for a $CO_2$-steam reforming process, in which both $CO_2$ and $H_2O$ react as oxidants of methane. In other embodiments, gaseous mixture 4 may be obtained from combining hydrocarbon-containing feedstock 1 with optional $CO_2$-containing oxidant 2, if, for example, hydrocarbon-containing feedstock 1 contains little $CO_2$ such as in the case of liquid hydrocarbons including naphtha boiling-range hydrocarbons and/or jet fuel boiling-range hydrocarbons, or otherwise in the case of some types of natural gas.

As another option, $H_2O$-containing oxidant 3 (e.g., as steam) may also be combined to form gaseous mixture 4, comprising methane and both $CO_2$ and $H_2O$ oxidants for a $CO_2$-steam reforming processes. Again, however, $H_2O$ may also be present in sufficient quantity in hydrocarbon-containing feedstock 1 and/or $CO_2$-containing oxidant 2, such that separate $H_2O$-containing oxidant 3 may not be necessary. As shown by dashed, double-headed arrows between hydrocarbon-containing feedstock 1, $CO_2$-containing oxidant 2, and $H_2O$-containing oxidant 3, it is clear that any of these may be combined prior to (e.g., upstream of) reforming reactor 5. According to a specific embodiment, FIG. 1B illustrates hydrocarbon-containing feedstock 1 being combined with optional $CO_2$-containing oxidant 2 and optional $H_2O$-containing oxidant 3 to provide gaseous mixture 4 both prior to (e.g., upstream of) reforming reactor 5, as well as within this reactor.

As described above, in embodiments in which gaseous mixture 4 comprises one or more hydrocarbons such as methane and $CO_2$, but not $H_2O$, the process may be considered a "dry reforming" process, whereas in embodiments in which gaseous mixture 4 comprises hydrocarbon(s) and $CO_2$, and further comprises $H_2O$ acting, in combination with the $CO_2$, as oxidants of the hydrocarbon(s) (e.g., such that at least respective oxidant portions of the $CO_2$ and $H_2O$ oxidize respective reactant portions of the hydrocarbon(s)), the process may be considered a "$CO_2$-steam reforming process." Reforming catalysts as described herein provide advantageous results in both dry reforming and $CO_2$-steam reforming, in terms of both activity and stability, as described above. Under reforming conditions provided in reforming reactor 5, gaseous mixture 4 is converted to synthesis gas product 7, which may, relative to gaseous mixture 4, be enriched in (i.e., have a higher concentration of) hydrogen and CO, and/or be depleted in (i.e., have a lower concentration of) $CO_2$, $H_2O$, methane, and/or other hydrocarbon(s) initially present in gaseous mixture 4.

An important methane-containing feedstock is natural gas, and particularly stranded natural gas, which, using known processes, is not easily converted to a synthesis gas product in an economical manner. Natural gas comprising a relatively high concentration of $CO_2$, for example at least about 10 mol-% or even at least about 25 mol-%, represents an attractive methane-containing feedstock, since processes as described herein do not require the removal of $CO_2$ (e.g., by scrubbing with an amine solution), in contrast to conventional steam reforming, and in fact utilize $CO_2$ as a reactant. Other methane-containing feedstocks may comprise methane obtained from coal or biomass (e.g., lignocellulose or char) gasification, from a biomass digester, or as an effluent from a renewable hydrocarbon fuel (biofuel) production processes (e.g., a pyrolysis process, such as a hydropyrolysis processes, or a fatty acid/triglyceride hydroconversion processes). Further methane-containing feedstocks may comprise methane obtained from a well head or an effluent of an industrial process including a petroleum refining process (as a refinery off gas), an electric power production process, a steel manufacturing process or a non-ferrous manufacturing process, a chemical (e.g., methanol) production process, or a coke manufacturing process. Generally, any process gas known to contain a hydrocarbon (e.g., a $C_1$-$C_3$ hydrocarbon) and $CO_2$ may provide all or a portion of the gaseous mixture as described herein, or at least all or a portion of the methane-containing feedstock as a component of this mixture. If the methane-containing feedstock comprises methane obtained from a renewable resource (e.g., biomass), for example methane from a process stream obtained by hydropyrolysis as described in U.S. Pat. No. 8,915,981 assigned to Gas Technology Institute, then processes described herein may be used to produce renewable synthesis gas products (i.e., comprising renewable CO) that, in turn, can be further processed to provide renewable hydrocarbon-containing fuels, fuel blending components, and/or chemicals. Accordingly, the methane-containing feedstock may therefore comprise methane from a non-renewable source (e.g., natural gas) and/or methane from a renewable source (e.g., biomass), with the latter source imparting an overall reduction in the carbon footprint associated with the synthesis gas product and downstream products. As further described herein, natural gas and/or other methane-containing feedstocks, may be, but need not be, pretreated to remove $H_2S$ and other sulfur-bearing contaminants, prior to dry reforming or $CO_2$-steam reforming.

Like the methane-containing feedstock (or hydrocarbon-containing feedstock generally), and particularly in view of the sulfur tolerance of reforming catalysts as described herein, other components of the gaseous mixture, including the $CO_2$-containing oxidant and/or $H_2O$-containing oxidant, may be obtained from a wide variety of sources. Advantageously, such sources include waste gases that are regarded as having little or no economic value, and that may additionally contribute to atmospheric $CO_2$ levels. For example, the $CO_2$-containing oxidant may comprise an industrial process waste gas that is obtained from a steel manufacturing process or a non-ferrous product manufacturing process. Other processes from which all or a portion of the $CO_2$-containing oxidant may be obtained include petroleum refining processes, renewable hydrocarbon fuel (biofuel) production processes (e.g., a pyrolysis process, such as a hydropyrolysis processes, or a fatty acid/triglyceride hydroconversion processes), coal and biomass gasification processes, electric power production processes, carbon black production processes, ammonia production processes, methanol production processes, and coke manufacturing processes.

As described above, the methane-containing feedstock (or hydrocarbon-containing feedstock generally) may itself provide the gaseous mixture for a dry reforming process or a $CO_2$-steam reforming process, i.e., without the addition of a separate $CO_2$-containing oxidant and/or a separate $H_2O$-containing oxidant, if sufficient $CO_2$ and/or $H_2O$ are already present in this mixture. Alternatively, the methane-containing feedstock (or hydrocarbon-containing feedstock generally), may be combined with only one of a $CO_2$-containing oxidant or $H_2O$-containing oxidant to provide a suitable gaseous mixture. For example, steam (as the $H_2O$-containing oxidant) may be combined with a methane-containing feedstock further comprising $CO_2$, to provide a gaseous mixture suitable for a $CO_2$-steam reforming process.

A representative methane-containing feedstock further comprising $CO_2$ in an amount particularly suitable for providing the gaseous mixture for a $CO_2$-steam reforming process described herein is a hydropyrolysis gaseous mixture obtained from biomass hydropyrolysis and having (i) a methane concentration of generally about 3 mol-% to about 45 mol-% (e.g., about 5 mol-% to about 25 mol-% or about 7 mol-% to about 15 mol-%), (ii) ethane and propane concentrations each of generally about 1 mol-% to about 35 mol-% (e.g., about 2 mol-% to about 25 mol-% each or about 3 mol-% to about 15 mol-% each), and (iii) a $CO_2$ concentration of generally about 10 mol-% to about 75 mol-% (e.g., about 12 mol-% to about 55 mol-% or about 15 mol-% to about 35 mol-%). The substantial balance of the hydropyrolysis gaseous mixture may be water vapor. However, depending on the actual amount of water vapor, an $H_2O$-containing oxidant may optionally be combined with the hydropyrolysis gaseous mixture to provide the gaseous mixture to a $CO_2$-steam reforming reactor with a desired molar $H_2O:CO_2$ ratio. In this case, the $H_2O$-containing oxidant may be readily available as a condensed aqueous phase that is separated from the substantially fully deoxygenated hydrocarbon liquid generated from the hydropyrolysis of biomass (e.g., a hydrocarbon-containing liquid having a total oxygen content of less than about 2% by weight, or less than about 1% by weight).

Another example of a representative methane-containing feedstock further comprising $CO_2$, in an amount particularly suitable for providing the gaseous mixture for a $CO_2$-steam reforming process described herein, is natural gas comprising $CO_2$ at a concentration of generally about 3 mol-% to about 35 mol-% (e.g., about 5 mol-% to about 30 mol-% or about 10 mol-% to about 25 mol-%) and methane at a concentration of generally about 65 mol-% to about 98 mol-% (e.g., about 70 mol-% to about 95 mol-% or about 75 mol-% to about 90 mol-%). Other hydrocarbons (e.g., ethane and propane), as well as nitrogen, may be present in minor amounts. An $H_2O$-containing oxidant may optionally be combined with this methane-containing feedstock to provide the gaseous mixture to a $CO_2$-steam reforming reactor with a desired molar $H_2O:CO_2$ ratio.

Another example of a representative methane-containing feedstock further comprising $CO_2$, in an amount particularly suitable for providing the gaseous mixture for a $CO_2$-steam reforming process described herein, is biogas obtained from the bacterial digestion of organic waste, such as from anaerobic digestion processes and from landfills. Biogas contains methane at a concentration of generally about 35 mol-% to about 90 mol-% (e.g., about 40 mol-% to about 80 mol-% or about 50 mol-% to about 75 mol-%) and $CO_2$ at a concentration of generally about 10 mol-% to about 60 mol-% (e.g., about 15 mol-% to about 55 mol-% or about 25 mol-% to about 50 mol-%). The gases $N_2$, $H_2$, $H_2S$, and $O_2$ may be present in minor amounts (e.g., in a combined amount of less than 20 mol-%, or less than 10 mol-%). An $H_2O$-containing oxidant may optionally be combined with this methane-containing feedstock to provide the gaseous mixture to a $CO_2$-steam reforming reactor with a desired molar $H_2O:CO_2$ ratio.

Another example of a representative methane-containing feedstock further comprising $CO_2$, in an amount particularly suitable for providing the gaseous mixture for a $CO_2$-steam reforming process described herein, is a hydrogen-depleted PSA tail gas, for example obtained from a hydrogen production processes involving SMR, as described above. This stream may have (i) a methane concentration of generally about 5 mol-% to about 45 mol-% (e.g., about 10 mol-% to about 35 mol-% or about 15 mol-% to about 25 mol-%), (ii) a $CO_2$ concentration of generally about 20 mol-% to about 75 mol-% (e.g., about 25 mol-% to about 70 mol-% or about 35 mol-% to about 60 mol-%), and (iii) an $H_2$ concentration of generally about 10 mol-% to about 45 mol-% (e.g., about 15 mol-% to about 40 mol-% or about 20 mol-% to about 35 mol-%). The balance of this stream may comprise predominantly water vapor and/or CO. An $H_2O$-containing oxidant may optionally be combined with this methane-containing feedstock to provide the gaseous mixture to a $CO_2$-steam reforming reactor with a desired molar $H_2O:CO_2$ ratio.

Another example of a representative methane-containing feedstock further comprising $CO_2$ in an amount particularly suitable for providing the gaseous mixture for a $CO_2$-steam reforming process described herein is a gaseous effluent from a bacterial fermentation that is integrated with a hydrogen production process, as described above. This stream may have (i) a methane concentration of generally about 5 mol-% to about 55 mol-% (e.g., about 5 mol-% to about 45 mol-% or about 10 mol-% to about 40 mol-%), (ii) a $CO_2$ concentration of generally about 5 mol-% to about 75 mol-% (e.g., about 5 mol-% to about 60 mol-% or about 10 mol-% to about 50 mol-%), and (iii) an $H_2$ concentration of generally about 5 mol-% to about 40 mol-% (e.g., about 5 mol-% to about 30 mol-% or about 10 mol-% to about 25 mol-%). The balance of this stream may comprise predominantly water vapor and/or CO. An $H_2O$-containing oxidant may optionally be combined with this methane-containing feedstock to provide the gaseous mixture to a $CO_2$-steam reforming reactor with a desired molar $H_2O:CO_2$ ratio.

In representative embodiments, according to FIGS. 1A and 1B, gaseous mixture 4 comprising a hydrocarbon and $CO_2$ may be contacted with reforming catalyst 6 in a batchwise or discontinuous operation, but preferably the dry reforming or $CO_2$-steam reforming process is performed continuously with flowing streams of the gaseous mixture 4 or components thereof (e.g., hydrocarbon-containing feedstock 1, $CO_2$-containing oxidant 2, and/or $H_2O$-containing oxidant 3 as described herein), to improve process efficiency. For example, contacting may be performed by continuously flowing the gaseous mixture 4 (e.g., as a combined reforming reactor feed stream of any of these components in combination) through the reforming reactor 5 and reforming catalyst 6 under reforming conditions (e.g., conditions within a reforming reactor vessel and within a bed of the reforming catalyst that is contained in the vessel) that include a suitable flow rate. In particular embodiments, the reforming conditions may include a weight hourly space velocity (WHSV) generally from about 0.05 $hr^{-1}$ to about 10 $hr^{-1}$, typically from about 0.1 $hr^{-1}$ to about 4.0 $hr^{-1}$, and often from about 0.3 $hr^{-1}$ to about 2.5 $hr^{-1}$. As is understood in the art, the WHSV is the weight flow of a total feed (e.g. the gaseous mixture) to a reactor, divided by the weight of the catalyst in the reactor and represents the equivalent catalyst bed weights of the feed stream processed every hour. The WHSV is related to the inverse of the reactor residence time. The reforming catalyst 6 may be contained within reforming reactor 5 in the form of a fixed bed, but other catalyst systems are also possible, such as moving bed and fluidized bed systems that may be beneficial in processes using continuous catalyst regeneration.

Other reforming conditions, which are useful for either dry reforming or $CO_2$-steam reforming, include a temperature generally from about 649° C. (1200° F.) to about 816° C. (1500° F.). Processes described herein, by virtue of the high activity of the reforming catalyst in terms of reducing the activation energy barrier required for the use of $CO_2$ as an oxidant, can effectively oxidize methane and/or other hydrocarbons at significantly lower temperatures, compared to a representative conventional temperature of 950° C. (1742° F.) that is used for dry reforming or steam reforming. For example, in representative embodiments, the reforming conditions can include a temperature in a range from about 677° C. (1250° F.) to about 788° C. (1450° F.), or from about 704° C. (1300° F.) to about 760° C. (1400° F.). As described above, the presence of $H_2S$ and/or other sulfur-bearing contaminants in significant amounts (e.g., 100-1000 mol-ppm) may warrant increased temperatures, for example in a range from about 732° C. (1350° F.) to about 843° C. (1550° F.), or from about 760° C. (1400° F.) to about 816° C. (1500° F.), to maintain desired conversion levels (e.g., greater than about 85%). Yet other reforming conditions can include an above-ambient pressure, i.e., a pressure above a gauge pressure of 0 kPa (0 psig), corresponding to an absolute pressure of 101 kPa (14.7 psia). Because the reforming reactions make a greater number of moles of product versus moles of reactant, equilibrium is favored at relatively low pressures. Therefore, reforming conditions can include a gauge pressure generally from about 0 kPa (0 psig) to about 517 kPa (75 psig), typically from about 0 kPa (0 psig) to about 345 kPa (50 psig), and often from about 103 kPa (15 psig) to about 207 kPa (30 psig).

Advantageously, within any of the above temperature ranges, the high activity of the reforming catalyst can achieve a conversion of methane and/or other hydrocarbon(s) (e.g., a conversion of methane, a conversion of combined $C_1$-$C_3$ hydrocarbons, a conversion of combined $C_1$-$C_4$ hydrocarbons, a conversion of naphtha boiling-range hydrocarbons, a conversion of jet fuel boiling-range hydrocarbons, etc.) of at least about 80% (e.g., from about 80% to about 99%), at least about 85% (e.g., from about 85% to about 97%), or at least about 90% (e.g., from about 90% to about 99%), for example by adjusting the particular reforming reactor temperature or reforming catalyst bed temperature and/or other reforming conditions (e.g., WHSV and/or pressure) as would be appreciated by those having skill in the art, with knowledge gained from the present disclosure. Advantageously, reforming catalysts as described herein are sufficiently active to achieve a significant hydrocarbon (e.g., methane) conversion, such as at least about 85%, in a stable manner at a temperature of at most about 732° C. (1350T), or even at most about 704° C. (1300° F.). With respect to the oxidant reactants, a representative conversion of $CO_2$ is at least about 50% (e.g., from about 50% to about 75%), and a representative conversion of $H_2O$ is at least about 70% (e.g., from about 70% to about 90%), at the conversion levels described herein with respect to hydrocarbon(s). As is understood in the art, conversion of any particular compound (e.g., methane) or combination of compounds (e.g., $C_1$-$C_4$ hydrocarbons or $C_1$-$C_3$ hydrocarbons) can be calculated on the basis of:

$$100*(X_{feed}-X_{prod})/X_{feed},$$

wherein $X_{feed}$ is the total amount (e.g., total weight or total moles) of the compound(s) X in the gaseous mixture (e.g., combined reactor feed) provided to a reactor and $X_{prod}$ is the total amount of the compound(s) X in the synthesis gas product removed from the reactor. In the case of continuous processes, these total amounts may be more conveniently expressed in terms of flow rates, or total amounts per unit time (e.g., total weight/hr or total moles/hr). Other performance criteria that can be achieved using reforming catalysts and reforming conditions as described herein include a high hydrogen yield, or portion of the total hydrogen in the methane and/or other hydrogen-containing compounds (e.g., total hydrogen in the hydrocarbons such as $C_2$-$C_4$ hydrocarbons or $C_2$-$C_3$ hydrocarbons), in the gaseous mixture provided to the reactor, which is converted to $H_2$ in the synthesis gas product removed from the reactor. In representative embodiments, the hydrogen yield is at least about 70% (e.g., from about 70% to about 85%). As described above with respect to conversion, amounts provided to and removed from the reactor may be expressed in terms of flow rates.

As described above, further advantages associated with reforming processes, and particularly $CO_2$-steam reforming processes, as described herein, include favorable molar $H_2/CO$ ratios, as well as the ability to adjust these ratios, in the synthesis gas product. This has especially important implications for downstream processing via Fischer-Tropsch for the production of liquid hydrocarbons. The exact composition of the synthesis gas product depends on the composition of the feed (e.g., combined reforming reactor feed) or gaseous mixture, the reforming catalyst, and the reforming conditions.

In representative embodiments, the synthesis gas product, particularly in the case of a $CO_2$-steam reforming process, advantageously has a molar $H_2$:CO ratio that is near 2:1, for example generally in a range from about 1.5:1 to about 2.3:1, and typically from about 1.8:1 to about 2.2:1. The combined concentration of $1H_2$ and CO in this product is generally at least about 35 mol-% (or vol-%) (e.g., from about 35 mol-% to about 85 mol-%), typically at least about 50 mol-% (e.g., from about 50 mol-% to about 80 mol-%), and often at least about 60 mol-% (e.g., from about 60 mol-% to about 75 mol-%). As described above, the balance of the synthesis gas product may be substantially or all $CO_2$ and water, depending on the particular dry reforming or $CO_2$-steam reforming process, including the conditions of such process (e.g., conditions within the reforming reactor such as temperature, pressure, weight hourly space velocity, and reforming catalyst formulation) and the feed or gaseous mixture being reacted. In representative embodiments, $CO_2$ is present in the synthesis gas product in a concentration of generally less than about 45 mol-% (e.g., from about 5 mol-% to about 45 mol-%) and typically less than about 35 mol-% (e.g., from about 10 mol-% to about 35 mol-%). Water may be present in a concentration of generally less than about 20 mol-% (e.g., from about 1 mol-% to about 25 mol-%) and typically less than about 15 mol-% (e.g., from about 5 mol-% to about 15 mol-%). Minor amounts of unconverted hydrocarbons may also be present in the synthesis gas product. For example, a combined amount of $C_1$-$C_4$ hydrocarbons (e.g., a combined amount of methane, ethane, propane, and butane), which may possibly include only $C_1$-$C_3$ hydrocarbons, may be present in a concentration of less than about 5 mol-% and typically less than about 2 mol-%.

Integrated Processes Including Conversion Steps to Produce Liquid Hydrocarbons

Further representative processes use dry reforming or $CO_2$-steam reforming, as described herein, with additional process steps, such as converting $H_2$ and CO in the synthesis gas product in an FT synthesis stage, in order to provide a Fischer-Tropsch product (e.g., effluent from an FT reactor as described above) comprising hydrocarbons, including $C_4^+$ hydrocarbons representative of those present in liquid fuels such as gasoline, jet fuel, and/or diesel fuel. For example, a particular integrated process for producing $C_4^+$ hydrocarbons may comprise, in a reforming reactor of a reforming stage, converting methane and $CO_2$ in a gaseous mixture, such as any of the gaseous mixtures described herein, including gaseous mixtures that may comprise any methane-containing feedstock or other component of such gaseous mixture as described above, to produce a synthesis gas product as described above. This converting step may more particularly comprise contacting the gaseous mixture with a reforming catalyst, such as any of the reforming catalysts described herein, in a reforming reactor of a reforming stage to produce the synthesis gas product. The integrated process may further comprise, in an FT reactor of an FT synthesis stage downstream of the reforming stage, converting $H_2$ and CO in the synthesis gas product to hydrocarbons, including $C_4^+$ hydrocarbons (i.e., at least some hydrocarbons having four or more carbon atoms) that are provided in an FT product. As an optional step, and particularly in the case of the $C_4^+$ hydrocarbons in the FT product including a wax fraction comprising normal $C_{20}^+$ hydrocarbons (i.e., at least some normal or straight-chain hydrocarbons having 20 or more carbon atoms that are consequently solid at room temperature), the integrated process may further comprise, in a finishing reactor of a finishing stage downstream of the FT synthesis stage, converting at least a portion of the normal $C_{20}^+$ hydrocarbons to normal or branched $C_4$-$C_{19}$ hydrocarbons (i.e., to normal or branched hydrocarbons, at least some of which have 4 to 19 carbon atoms) that are provided in a hydroisomerization/hydrocracking product.

The term "stage" as used in "reforming stage," "FT synthesis stage," and "finishing stage," refers to reactor(s) used to carry out the reactions associated with these stages as described herein, as well as the catalyst(s) and conventional auxiliary equipment (e.g., sensors, valves, gauges, control systems, etc.) associated with the reactor(s). In some embodiments, and preferably, only a single reactor is needed for a given stage, i.e., a single reforming reactor, a single FT reactor, and/or a single finishing reactor. However, reactions associated with a given stage may also be carried out in more than one reactor, for example two reactors operating in parallel or in series.

Additional details and advantages, in representative integrated processes, of the reforming stage, FT synthesis stage, and optional finishing stage are provided below, with the understanding that integrated processes according to the present disclosure include those having any one of these additional details and/or advantages, or otherwise any combination of such details and/or advantages.

Reforming Stage

The reforming stage includes at least one, and typically only one, reforming reactor as described above, which may be a dry reforming reactor or a $CO_2$-steam reforming reactor, with the latter term indicating the presence of steam in the gaseous mixture. Gaseous mixtures that are converted in this stage are as described above, as well as representative reforming catalysts and their properties (e.g., activity, stability, tolerance to sulfur and higher molecular weight hydrocarbons, etc.), reforming conditions suitable for use in at least one reforming reactor, and performance criteria (conversion levels and product yields).

As described above, the gaseous mixture may be pretreated, upstream of the reforming reactor(s), to reduce the concentration of $H_2S$ and/or other sulfur-bearing contaminants, for example by contacting the gaseous mixture or any component thereof (e.g., the hydrocarbon-containing feedstock) with a suitable bed of sorbent or a liquid wash. Alternatively, a post-treatment (downstream of the reforming stage) of the synthesis gas product or possibly of the FT feed (e.g., following condensing of water from a cooled synthesis gas product to provide the FT feed) may be performed, for example in this manner, to reduce the concentration of $H_2S$ and/or other sulfur-bearing contaminants. The option to perform a step of removing sulfur-bearing contaminants either upstream or downstream of the reforming reactor(s) arises from the sulfur tolerance of reforming catalysts as described above, such that the protection of the reforming catalyst from sulfur poisoning may not be necessary, although protection of the FT catalyst may be necessary. Advantageously, if the concentration of $H_2S$ and/or other sulfur-bearing contaminants is reduced upstream of the reforming reactor(s) (e.g., an $H_2S$ removal pretreatment is performed on the gaseous mixture), such pretreatment may be less rigorous and/or involve less gas removal, compared to conventional acid gas removal (e.g., using amine scrubbing) in which $CO_2$ would also normally be removed. The ability of reforming catalysts described herein to tolerate $CO_2$, and in fact utilize this gas as a reactant, can therefore allow for a reduction, or even the elimination, of conventional pretreatment steps. For example, a gaseous mixture comprising natural gas and having a high concentration of $CO_2$ (e.g., greater than 25 mol-% or greater than 30 mol-%), which may be due to the particular source of the natural gas, may be provided to the reforming reactor(s) without any pretreatment, or possibly with only a pretreatment for the removal of dust particles, such as by filtration.

As described above, the reforming stage produces a synthesis gas product comprising $H_2$ and CO, by virtue of reacting a hydrocarbon by dry reforming or by $CO_2$-steam reforming. As further described above, in view of the favorable ranges of molar $H_2$:CO ratios (e.g., encompassing 2:1 in the case of $CO_2$-steam reforming) of the synthesis gas product that may be obtained, advantageously some or all of the synthesis gas product may be used directly in the FT synthesis stage, without any intervening operation that would impact the molar $H_2$:CO ratio (e.g., by the addition, removal, or conversion of components that would alter this ratio, such as by the use of a separate water-gas shift reaction or reverse water-gas shift reaction). Further advantages associated with the composition of the synthesis gas product are described according to embodiments presented herein and relating to the downstream processing of this product.

FT Synthesis Stage

In the FT reactor(s) or overall FT synthesis stage, at least a portion of the $H_2$ and CO in the synthesis gas product are converted to hydrocarbons, according to the Fischer-Tropsch (FT) synthesis reaction given above. In particular, an FT feed comprising some or all of the synthesis gas product, optionally following one or more intervening operations such as cooling, heating, pressurizing, depressurizing, separation of one or more components (e.g., removal of condensed water), addition of one or more components (e.g., addition of $H_2$ and/or CO to adjust the molar $H_2$:CO ratio of the FT feed relative to that of the synthesis gas product), and/or reaction of one or more components (e.g., reaction of $H_2$ and/or CO using a separate water-gas shift reaction or reverse water-gas shift reaction), is provided to the FT reactor(s) of the FT synthesis stage. In view of the temperatures and pressures typically used in the FT reactor(s) of the FT synthesis stage relative to those used in the reforming reactor(s) of the reforming stage, the synthesis gas product may be cooled, separated from condensed water, and pressurized. In some embodiments, these may be the only intervening operations to which the synthesis gas product is subjected, to provide the FT feed. In other embodiments, cooling and pressurizing may be the only intervening operations. In yet other embodiments, intervening operations that may be omitted include drying of the synthesis gas product to remove vapor phase $H_2O$ (which is therefore different from condensing liquid phase $H_2O$ and can include, e.g., using a sorbent selective for water vapor, such as 5A molecular sieve) and/or $CO_2$ removal according to conventional acid gas treating steps (e.g., amine scrubbing). However, according to some embodiments, $CO_2$ removal may be performed downstream of the reforming stage but upstream of the FT synthesis stage (e.g., as an intervening operation), in lieu of performing this $CO_2$ removal upstream of the reforming stage, as is conventionally practiced. Preferably, prior to the FT reactor(s), water produced in the reforming reactor is condensed from the synthesis gas product, and/or also preferably the molar $H_2$:CO ratio of the synthesis gas product is not adjusted. The use of no intervening operations between the reforming stage and the FT synthesis stage, limited intervening operations, and/or the omission or certain intervening operations, results in advantages associated with the overall simplification of the integrated process.

Conditions in the FT reactor(s) are suitable for the conversion of $H_2$ and CO to hydrocarbons, including $C_4^+$ hydrocarbons that are useful as liquid fuels or blending components of liquid fuels. In representative embodiments, FT reaction conditions (suitable for use in at least one FT reactor) can include a temperature in a range from about 121° C. (250° F.) to about 288° C. (550° F.), or from about 193° C. (380° F.) to about 260° C. (500° F.). Other FT reaction conditions can include a gauge pressure from about 689 kPa (100 psig) to about 3.44 MPa (500 psig), or from about 1.38 MPa (200 psig) to about 2.76 MPa (400 psig). One advantage over the use of an FT synthesis stage downstream of the reforming stage, relative to the downstream production of methanol and/or DME as described above, is the significantly reduced pressure (e.g., generally below about 3.44 MPa (500 psig) or typically below about 3.10 MPa (450 psig)) compared to these downstream processing alternatives.

In the FT reactor(s), the FT feed may be contacted with a suitable FT catalyst (e.g., bed of FT catalyst particles disposed within the FT reactor) under FT reaction conditions, which may include the temperatures and/or pressures as described above. Representative FT catalysts comprise one or more transition metals selected from cobalt (Co), iron (Fe), ruthenium (Ru), and nickel (Ni). A preferred FT catalyst comprises at least about 10 wt-% of the transition metal(s), and typically at least about 15 wt-% of the transition metal(s), on a solid support. The phrase "on a solid support" is intended to encompass catalysts in which the active metal(s) is/are on the support surface and/or within a porous internal structure of the support. Representative solid supports comprise one or more metal oxides, selected from the group consisting of aluminum oxide, silicon oxide, titanium oxide, zirconium oxide, magnesium oxide, strontium oxide, etc. The solid support may comprise all or substantially all (e.g., greater than about 95 wt-%) of the one or more of such metal oxides. Preferred FT catalysts comprise the transition metal cobalt (Co) in the above amounts (e.g., at least about 10 wt-%) on a support comprising aluminum oxide (alumina).

The FT catalysts and FT reaction conditions described herein are generally suitable for achieving a conversion of $H_2$ and/or CO ($H_2$ conversion or CO conversion) of at least about 20% (e.g., from about 20% to about 99% or from about 20% to about 75%), at least about 30% (e.g., from about 30% to about 95% or from about 30% to about 65%), or at least about 50% (e.g., from about 50% to about 90% or from about 50% to about 85%). These FT conversion levels may be based on $H_2$ conversion or CO conversion, depending on which reactant is stoichiometrically limited in the FT feed, considering the FT synthesis reaction chemistry, and these FT conversion levels may be calculated as described above. Preferably, these FT conversion levels are based on CO conversion. These FT conversion levels may be based on "per-pass" conversion, achieved in a single pass through the FT synthesis stage (e.g., an FT reactor of this stage), or otherwise based on overall conversion, achieved by returning a recycle portion of the FT product back to the FT synthesis stage (e.g., an FT reactor of this stage), as described in greater detail below.

Figure 2:
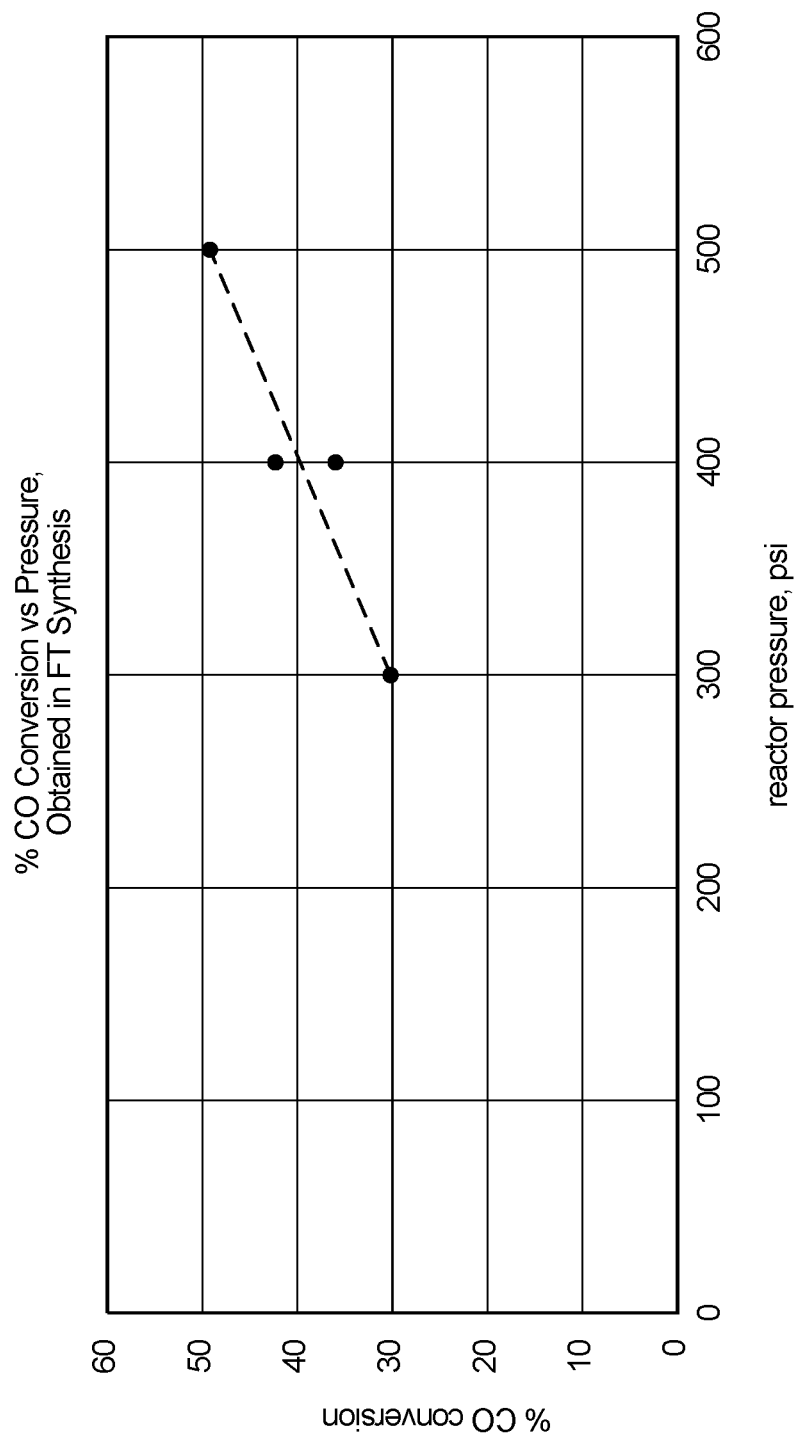
FIG. 2 illustrates the relationship between pressure in a Fischer-Tropsch (FT) reactor and the level of CO conversion obtained, with other operating conditions remaining constant.

A desired $H_2$ conversion and/or CO conversion in the FT reactor(s) may be achieved by adjusting the FT reaction conditions described above (e.g., FT reaction temperature and/or pressure), and/or adjusting the weight hourly space velocity (WHSV), as defined above. The FT reaction conditions may include a weight hourly space velocity (WHSV) generally from about 0.01 $hr^{-1}$ to about 10 $hr^{-1}$, typically from about 0.05 $hr^{-1}$ to about 5 $hr^{-1}$, and often from about 0.3 $hr^{-1}$ to about 2.5 $hr^{-1}$. The conversion level (e.g., CO conversion) may be increased, for example, by increasing pressure and decreasing WHSV, both of which have the effect of increasing reactant concentrations and reactor residence times. An example of the effect of pressure on the level of CO conversion achieved in a Fischer-Tropsch (FT) reactor, containing an FT catalyst as described herein and also while operating with other FT reaction conditions constant and within ranges as described above, is depicted in FIG. 2. The FT reaction conditions may optionally include returning a recycle portion of the FT product, exiting the FT reactor, back to the FT feed for combining with the FT feed, or otherwise back to the FT reactor itself. Recycle operation allows for operation at relatively low "per-pass" conversion through the FT reactor, while achieving a high overall conversion due to the recycle. In some embodiments, this low per-pass conversion may advantageously limit the quantity of high molecular weight hydrocarbons (e.g., normal $C_{20}^+$ hydrocarbons) that can be produced as part of the hydrocarbon product distribution obtained from the FT synthesis reaction.

Preferably, however, the FT reaction conditions include little or even no FT product recycle. For example, the FT reaction conditions may include a weight ratio of recycled FT product to FT feed (i.e., a "recycle ratio"), with this recycled FT product and FT feed together providing a combined feed to the FT reactor, of generally less than about 1:1, typically less than about 0.5:1, and often less than about 0.1:1. For example, the recycle ratio may be 0, meaning that no FT product recycle is used, such that the per-pass conversion is equal to the overall conversion. With such low recycle ratios, a relatively high per-pass $H_2$ conversion or CO conversion, such as at least about 50% (e.g., from about 50% to about 95%), at least about 70% (e.g., from about 70% to about 92%), or at least about 80% (e.g., from about 80% to about 90%), is desirable in view of process efficiency and economics. As the per-pass conversion level is increased, the distribution of hydrocarbons in the FT product is shifted to those having increased numbers of carbon atoms. This is advantageous in terms of the reduction in yield of light, $C_1$-$C_3$ hydrocarbons, having less value than the desired $C_4^+$ liquid hydrocarbons. In some embodiments, the $C_1$-$C_3$ hydrocarbon yield ("gaseous hydrocarbon yield"), or portion of the total carbon in the CO in the FT feed provided to an FT reactor, which is converted to $C_1$-$C_3$ hydrocarbons in the FT product removed from the reactor, is less than about 30% (e.g., from about 1% to about 30%) or even less than about 20% (e.g., from about 3% to about 20%). As described above with respect to conversion, amounts provided to and removed from the reactor may be expressed in terms of flow rates.

Embodiments of the invention are therefore directed to a process for producing $C_4^+$ hydrocarbons from a synthesis gas comprising $H_2$ and CO, for example a synthesis gas product, or an FT feed, as described above. The synthesis gas product or FT feed may generally be produced by reforming (conventional reforming, dry reforming, or $CO_2$-steam reforming). The process comprises contacting the synthesis gas with an FT catalyst comprising at least about 10 wt-% Co and/or optionally other transition metal(s) described above, on a solid support, for example a refractory metal oxide such as alumina. The process comprises converting $H_2$ and CO in the synthesis gas to hydrocarbons, including $C_4^+$ hydrocarbons, provided in an FT product, for example as described herein.

Advantageously, in the absence of FT product recycle, compression costs are saved and the overall design of the integrated process is simplified. To the extent that this requires an increase in the per-pass conversion and associated shift in the distribution of hydrocarbons in the FT product toward those having increased numbers of carbon atoms, including normal $C_{20}^+$ hydrocarbons that are undesirable, it should be appreciated that aspects of the invention are associated with the discovery of important, further downstream processing strategies for converting these normal $C_{20}^+$ hydrocarbons to normal and/or branched $C_4$-$C_{19}$ hydrocarbons, which contribute to the yield of desired naphtha boiling-range hydrocarbons, jet fuel boiling-range hydrocarbons, and/or diesel boiling-range hydrocarbons. An optional further downstream processing stage, namely a finishing stage for carrying out this conversion, is described below.

Finishing Stage

An optional finishing stage may be desirable, as described above, in embodiments in which the $C_4^+$ hydrocarbons in the FT product include normal $C_{20}^+$ hydrocarbons. In particular, a wax fraction of the $C_4^+$ hydrocarbons may comprise such high carbon number hydrocarbons, with this wax fraction referring to hydrocarbons that are solid at room temperature and that not only represent a loss in yield of hydrocarbons having greater utility as liquid fuels, but also pose significant problems in terms of causing detrimental wax accumulation within process piping, in addition to difficulties associated with transporting and blending.

In the finishing reactor(s) of a finishing stage, at least a portion of the normal $C_{20}^+$ hydrocarbons in the FT product are converted to normal and/or branched $C_4$-$C_{19}$ hydrocarbons, according to hydroisomerization and hydrocracking reactions occurring in the reactor(s). In particular, a finishing feed may comprise some or all of the FT product, optionally following one or more intervening operations such as cooling, heating, pressurizing, depressurizing, separation of one or more components, addition of one or more components, and/or reaction of one or more components. In view of the temperatures and pressures typically used in the finishing reactor(s) of the finishing stage relative to those used in the FT reactor(s) of the FT synthesis stage, the FT product may be heated, prior to conversion of normal $C_{20}^+$ hydrocarbons in the FT product in the finishing stage, to a temperature suitable for a finishing reactor used in this stage, as described herein. In some embodiments, this heating may be the only intervening operation to which the FT product is subjected, to provide the finishing feed. Alternatively, for even greater operational simplicity and efficiency, even this heating may be omitted, in view of the possibility for the FT reaction conditions to include a temperature that is the same or substantially the same as (e.g., within about 10° C. (18° F.) of) that used in the downstream finishing stage, for example within a temperature range as described below with respect to the finishing reaction conditions. In other embodiments, intervening operations that may be omitted include pressurizing and depressurizing, as it has been discovered that finishing reaction conditions can advantageously include a same or substantially same pressure as described above with respect to FT reaction conditions. For example, a pressure in a finishing reactor can be the same pressure as in an upstream FT reactor, reduced by a nominal pressure drop associated with the piping and possibly other process equipment between these reactors. Therefore, costs for pressurization (compression) or depressurization (expansion) of the FT product, upstream of the finishing reactor, can be advantageously avoided. As with intervening operations between the reforming stage and FT synthesis stage, the use of no intervening operations, limited intervening operations, and/or the omission of certain intervening operations between the FT synthesis stage and finishing stage results in advantages associated with the overall simplification of the integrated process. Particular advantages result, for example, if all or substantially all of the synthesis gas product is used in the FT feed and/or all or substantially all of the FT product is used in the finishing feed. In other embodiments, all or substantially all of the synthesis gas product, except for a condensed water-containing portion, is used in the FT feed and/or all or substantially all of the FT product is used in the finishing feed.

Conditions in the finishing reactor(s) are suitable for the conversion of normal $C_{20}^+$ hydrocarbons to $C_4$-$C_{19}$ hydrocarbons, according to finishing reactions that include or possibly consist of hydroisomerization and/or hydrocracking reactions. A finishing reactor may be incorporated into an FT reactor, for example by using a bed of finishing catalyst directly following a bed of FT catalyst within a single vessel, or otherwise interspersing the two catalyst types within a single vessel. However, generally the use of at least one separate finishing reactor (e.g., in a separate finishing reactor vessel) is preferred, such that finishing reaction conditions can be maintained independently of FT reaction conditions as described above. A separate finishing reactor may be advantageous, for example, for (i) maintaining the finishing catalyst in a different reactor type, compared to the FT reactor, such as maintaining the finishing catalyst in a fixed bed reactor that is normally simpler in design compared to the FT reactor, as a fixed bed reactor normally does involve not the same design constraints in terms of the ability to remove reaction heat, (ii) removing and/or replacing the finishing catalyst at times that do not necessarily coincide with (e.g., at differing intervals relative to) removing and/or replacing the FT catalyst, and/or (iii) operating the finishing reactor at a different temperature (e.g., at a higher temperature) compared to the FT reactor. With respect to the use of a separate finishing reactor, it may be important to maintain the FT product (or at least any portion of this product used in the finishing reactor), from the outlet (effluent) of the FT reactor to the inlet of the finishing reactor, at an elevated temperature to avoid deposition of any normal $C_{20}^+$ hydrocarbons, and other hydrocarbons having similarly high melting temperatures, as solid wax. Such deposition can result not only in losses of desired product that would otherwise be produced from conversion in the finishing stage, but also in the plugging and/or fouling of process equipment, leading to operational failure. The use of a finishing reactor may also be simplified if condensation of any normal $C_{20}^+$ hydrocarbons is avoided, i.e., if all or substantially all of the FT product is maintained in the vapor phase from the outlet of the FT reactor to the inlet of the finishing reactor. For example, to avoid deposition and/or condensation, the FT product may be maintained at a temperature of at least about 66° C. (150° F.), at least about 121° C. (250° F.), at least about 216° C. (420° F.), or even at least about 327° C. (620° F.), from the effluent of the FT reactor to the inlet of the finishing reactor, such as in the case of heating the FT product from this temperature to a temperature suitable for a finishing reactor, as described herein.

In representative embodiments, finishing reaction conditions (suitable for use in at least one finishing reactor) can include a temperature in a range from about 232° C. (450° F.) to about 399° C. (750° F.), or from about 304° C. (580° F.) to about 371° C. (700° F.). Other finishing reaction conditions can include a gauge pressure from about 621 kPa (90 psig) to about 3.38 MPa (490 psig), or from about 2.00 MPa (290 psig) to about 3.10 MPa (450 psig).

In the finishing reactor(s), the finishing feed may be contacted with a suitable finishing catalyst (e.g., bed of finishing catalyst particles disposed within the finishing reactor) under finishing reaction conditions, which may include the temperatures and/or pressures described above. As also described above, the finishing catalyst preferably has activity for hydrocracking and/or hydroisomerization of normal $C_{20}^+$ hydrocarbons present in the FT product. These hydrocarbons, characteristic of solid wax, result from the carbon number distribution of normal hydrocarbons produced by the Fischer-Tropsch reaction chemistry, in conjunction with $C_4$-$C_{19}$ hydrocarbons that are more desirable as components of liquid fuels, as described herein. As understood in the art, hydroisomerization refers to reactions of normal hydrocarbons in the presence of hydrogen to produce branched hydrocarbons. Hydrocracking refers to reactions of hydrocarbons with hydrogen to produce hydrocarbons having a lower number of carbon atoms and consequently a lower molecular weight. Hydroisomerization is beneficial for improving characteristics of hydrocarbons having a lower number of carbon atoms (e.g., $C_4$-$C_{19}$ hydrocarbons) and useful as components of liquid fuels, which hydrocarbons may be present in the finishing feed and/or FT product or which may be produced by hydrocracking in the finishing reactor(s). These characteristics include a higher octane number (e.g., research octane number and/or motor octane number) of naphtha boiling-range hydrocarbons present in the finishing product, relative to that of the finishing feed and/or FT product. These characteristics also include a reduced pour point of diesel boiling-range hydrocarbons present in the finishing product, relative to that of the finishing feed and/or FT product. Hydrocracking is beneficial for its overall impact on the carbon number distribution of the finishing feed, which may correspond to that of the FT product, and in particular for reducing the percentage by weight of, and possibly eliminating, normal $C_{20}^+$ hydrocarbons present in finishing feed and/or FT product. These hydrocarbons, being solid at room temperature, hinder the ability of products containing such hydrocarbons to be transported via a normal pipeline.

As both hydroisomerization and hydrocracking reactions require hydrogen, in preferred embodiments this hydrogen is present in the finishing feed and/or FT product to the finishing reactor. For example, hydrogen in the synthesis gas product that is unconverted in the downstream FT reactor may allow operation of the finishing reactor without the need for a supplemental source of hydrogen being added to the finishing reactor or downstream of the FT reactor. According to some embodiments, hydrogen is present in the finishing feed and/or FT product at a concentration of least about 20 mol-% (e.g., from about 20 mol-% to about 75 mol-%), at least about 30 mol-% (e.g., from about 30 mol-% to about 65 mol-%), or at least about 40 mol-% (e.g., from about 40 mol-% to about 60 mol-%), without the introduction of a supplemental source of hydrogen, beyond the hydrogen produced in the reforming stage and/or present in the synthesis gas product. According to other embodiments, a supplemental source of hydrogen, added to a finishing reactor, or upstream of a finishing reactor, of the finishing stage (e.g., downstream of an FT reactor of the FT synthesis stage), may be used to achieve such hydrogen concentrations. A representative supplemental source of hydrogen is hydrogen that has been purified (e.g., by PSA or membrane separation) or hydrogen that is impure (e.g., syngas).

Representative finishing catalysts, to the extent that they have activity for converting wax, i.e., hydroisomerization and hydrocracking activity with respect to normal $C_{20}^+$ hydrocarbons as described above, may also be referred to as dewaxing catalysts. Examples of finishing or dewaxing catalysts comprise at least one dewaxing active (e.g., hydroisomerization and/or hydrocracking active) metal on a solid support. The phrase "on a solid support" is intended to encompass catalysts in which the active metal(s) is/are on the support surface and/or within a porous internal structure of the support. Representative dewaxing active metals may be selected from the Groups 12-14 of the Periodic Table, such as from Group 13 or Group 14 of the Periodic Table. A particular dewaxing active metal is gallium. The at least one dewaxing active metal may be present in an amount, for example, from about 0.1 wt-% to about 3 wt-%, or from about 0.5 wt-% to about 2 wt-%, based on the weight of the dewaxing catalyst. If a combination of dewaxing active metals are used, such as a combination of metals selected from Groups 12-14 of the Periodic Table, then such metals may be present in a combined amount within these ranges. Generally, the dewaxing catalysts may comprise no metal(s) on the support in an amount, or combined amount, of greater than about 1 wt-%, or greater than about 0.5 wt-%, based on the weight of the dewaxing catalyst, other than the dewaxing active metal(s) described above (e.g., no metals other than metals of Groups 12-14 of the Periodic Table, no metals other than metals of Groups 13 or Group 14 of the Periodic Table, or no metals other than gallium, in this amount or combined amount). Preferably, the dewaxing catalyst comprises no metals on the support, other than the dewaxing active metal(s) described above (e.g., no metals other than metals of Groups 12-14 of the Periodic Table, no metals other than metals of Groups 13 or Group 14 of the Periodic Table, or no metals other than gallium).

In order to promote hydrocracking activity, the solid support of the finishing catalyst or dewaxing catalyst may be more particularly a solid acidic support. The acidity of a support may be determined, for example, by temperature programmed desorption (TPD) of a quantity of ammonia (ammonia TPD), from an ammonia-saturated sample of the support, over a temperature from 275° C. (527° F.) to 500° C. (932° F.), which is beyond the temperature at which the ammonia is physisorbed. The quantity of acid sites, in units of millimoles of acid sites per gram (mmol/g) of support, therefore corresponds to the number of millimoles of ammonia that is desorbed per gram of support in this temperature range. A representative solid support comprises a zeolitic or non-zeolitic molecular sieve and has at least about 15 mmol/g (e.g., from about 15 to about 75 mmol/g) of acid sites, or at least about 25 mmol/g (e.g., from about 25 to about 65 mmol/g) of acid sites, measured by ammonia TPD. In the case of zeolitic molecular sieves, acidity is a function of the silica to alumina ($SiO_2/Al_2O_3$) molar framework ratio, and, in embodiments in which the solid support comprises a zeolitic molecular sieve (zeolite), its silica to alumina molar framework ratio may be less than about 60 (e.g., from about 1 to about 60), or less than about 40 (e.g., from about 5 to about 40). Particular solid supports may comprise one or more zeolitic molecular sieves (zeolites) having a structure type selected from the group consisting of FAU, FER, MEL, MTW, MWW, MOR, BEA, LTL, MFI, LTA, EMT, ERI, MAZ, MEI, and TON, and preferably selected from one or more of FAU, FER, MWW, MOR, BEA, LTL, and MFI. The structures of zeolites having these and other structure types are described, and further references are provided, in Meier, W. M, et al., *Atlas of Zeolite Structure Types*, 4$^{th}$ Ed., Elsevier: Boston (1996). Specific examples include zeolite Y (FAU structure), zeolite X (FAU structure), MCM-22 (MWW structure), and ZSM-5 (MFI structure), with ZSM-5 being exemplary.

Solid supports other than zeolitic and non-zeolitic molecular sieves include metal oxides, such as any one or more of silica, alumina, titania, zirconia, magnesium oxide, calcium oxide, strontium oxide, etc. In representative embodiments, the solid support may comprise (i) a single type of zeolitic molecular sieve, (ii) a single type of non-zeolitic molecular sieve, or (iii) a single type of metal oxide, wherein (i), (ii), or (iii) is present in an amount greater than about 75 wt-% (e.g., from about 75 wt-% to about 99.9 wt-%) or greater than about 90 wt-% (e.g., from about 90 wt-% to about 99 wt-%), based on the weight of the dewaxing catalyst. Other components of the support, such as binders and other additives, may be present in minor amounts, such as in an amount, or combined amount, of less than about 10 wt-% (e.g., from about 1 wt-% to about 10 wt-%), based on the weight of the dewaxing catalyst.

An exemplary dewaxing catalyst comprises gallium as the dewaxing active metal, present in an amount as described above (e.g., from about 0.5 wt-% to about 2 wt-%, such as about 1 wt-%, based on the weight of the dewaxing catalyst) on a support comprising, or possibly consisting essentially of, ZSM-5. Representative silica to alumina molar framework ratios of the ZSM-5 are describe above.

Finishing or dewaxing catalysts and finishing reaction conditions described herein are generally suitable for achieving a conversion of normal $C_{20}^+$ hydrocarbons (e.g., normal $C_{20}$-$C_{60}$ hydrocarbons) of at least about 80% (e.g., from about 80% to about 100%), at least about 85% (e.g., from about 85% to about 98%), or at least about 90% (e.g., from about 90% to about 95%). Such high conversion levels are important for improving the quality of the FT product, especially in terms of its ability to be transportable (e.g., via pipeline) as a liquid fuel, without the need for separation or conversion of solid wax. The conversion of normal $C_{20}^+$ hydrocarbons to lower molecular weight, $C_4$-$C_{19}$ hydrocarbons also improves the overall yield of these hydrocarbons, compared to the operation of the FT synthesis stage in isolation. Preferably, in the finishing stage (e.g., in a finishing reactor of this stage), at least about 75% (e.g., from about 75% to about 100%), at least about 85% (e.g., from about 85% to about 98%), or at least about 90% (e.g., from about 90% to about 97%) of the normal $C_{20}^+$ hydrocarbons in the FT product are converted to $C_4$-$C_{19}$ hydrocarbons. That is, the yields of $C_4$-$C_{19}$ hydrocarbons from the conversion of normal $C_{20}^+$ hydrocarbons in the finishing stage are within these ranges. Preferably, the finishing product (or hydroisomerization/hydrocracking product of the finishing reactor) comprises less than about 2 wt-%, or even less than about 1 wt-% of hydrocarbons that are solid at room temperature (e.g., normal $C_{20}^+$ hydrocarbons). In representative embodiments, normal $C_{20}^+$ hydrocarbons are converted (e.g., at complete or substantially complete conversion and/or within the conversion ranges given above) in the finishing stage (e.g., in at least one finishing reactor of this stage), with a yield of (i) isoparaffinic (branched) hydrocarbons from about 25% to about 70%, or from about 40% to about 60%, (ii) aromatic hydrocarbons from about 10% to about 35% or from about 15% to about 25%, (iii) gasoline boiling-range hydrocarbons from about 50% to about 95% or from about 70% to about 90%, (iv) diesel boiling-range hydrocarbons from about 5% to about 45% or from about 10% to about 30%, and/or (v) VGO boiling-range hydrocarbons of less than about 1% or less than about 0.5%, with these yields referring to the percentage of the total carbon in the normal $C_{20}^+$ hydrocarbons in the finishing feed provided to a finishing reactor, which is converted to these components in the finishing product. Advantageously, isoparaffinic hydrocarbons improve the quality of diesel boiling-range hydrocarbons by reducing both the pour point and the cloud point of this fraction. Both isoparaffinic hydrocarbons and aromatic hydrocarbons improve the quality of gasoline boiling-range hydrocarbons by increasing the octane number (e.g., research octane number and/or motor octane number) of this fraction. In representative embodiments, the gasoline boiling-range hydrocarbons obtained from conversion of normal $C_{20}^+$ hydrocarbons in the finishing stage have a research octane number of at least about 75 (e.g., from about 75 to about 85).

As described above, conversion levels of normal $C_{20}^+$ hydrocarbons in the finishing stage (e.g., in the at least one finishing reactor of this stage) may be below 100% and therefore allow for a portion of these normal $C_{20}^+$ hydrocarbons in the finishing feed to remain unconverted. To achieve complete conversion of normal $C_{20}^+$ hydrocarbons, such as complete conversion to $C_4$-$C_{19}$ hydrocarbons and/or branched $C_{20}^+$ hydrocarbons, finishing reaction conditions may be made more severe, such as by increasing temperature, increasing pressure, and/or decreasing WHSV.

However, it is to be understood that complete conversion of normal $C_{20}^+$ hydrocarbons is not a requirement to achieve complete "dewaxing" of the FT product and/or finishing feed, in the sense of providing a finishing product that is free of solid phase hydrocarbons and therefore easily transportable as a liquid fuel, according to preferred embodiments. Incomplete conversion of normal $C_{20}^+$ hydrocarbons (such as achieving conversion levels within certain ranges described above) can nonetheless provide a finishing product in which sufficient products resulting from the conversion of normal $C_{20}^+$ hydrocarbons, namely (i) sufficient non-normal $C_{20}^+$ hydrocarbons (e.g., branched $C_{20}^+$ hydrocarbons) having melting points below room temperature (20° C.) and/or (ii) sufficient $C_4$-$C_{19}$ hydrocarbons, are present in the finishing product, to the extent that any unconverted normal $C_{20}^+$ hydrocarbons are dissolved at room temperature in the finishing product comprising (i) and (ii).

Embodiments of the invention are therefore directed to the use of a finishing stage, following an FT synthesis stage, to improve the overall selectivities to, and yields of, desired products and/or decrease the overall selectivities to, and yields of, undesired products (particularly wax), relative to the FT synthesis stage in the absence of the finishing stage (i.e., relative to a baseline FT synthesis stage or FT synthesis reaction). For example, the finishing stage can beneficially convert some or all wax (e.g., at the conversion levels of normal $C_{20}^+$ hydrocarbons as described above) produced by the FT synthesis reaction, thereby decreasing the selectivity to (and/or yield of) wax, in the combined FT synthesis and finishing stages relative to the baseline FT synthesis stage. In representative embodiments, the selectivity to (and/or yield of) wax is decreased from a value from about 10% to about 50%, such as from about 20% to about 45%, in the baseline FT synthesis stage to a value from about 0% to about 10%, such as from about 0.5% to about 5%, in the combined FT synthesis and finishing stages. Preferably, this selectivity to (and/or yield of) wax is decreased to less than about 0.5%. As described above, small quantities of wax in the finishing product can be acceptable to the extent that any unconverted normal $C_{20}^+$ hydrocarbons, and/or any hydrocarbons generally that melt above room temperature, are present in an amount that is below their solubility in the finishing product (i.e., in an amount such that they may be completely dissolved in the finishing product). In other representative embodiments, the selectivity to (and/or yield of) of $C_4$-$C_{19}$ liquid hydrocarbons is increased from a value from about 15% to about 45%, such as from about 20% to about 35%, in the baseline FT synthesis stage to a value from about 40% to about 75%, such as from about 50% to about 70%, in the combined FT synthesis and finishing stages. Selectivities to wax or $C_4$-$C_{19}$ hydrocarbons, with respect to the baseline FT synthesis stage and combined FT synthesis and finishing stages, are based on the percentage of carbon in CO converted by FT, which results in wax or $C_4$-$C_{19}$ liquid hydrocarbons, respectively. Yields of wax or $C_4$-$C_{19}$ hydrocarbons, with respect to the baseline FT synthesis stage and combined FT synthesis and finishing stages, are based on the percentage of carbon in CO introduced to the FT synthesis stage (e.g., CO introduced with the FT feed, whether converted or unconverted), which results in wax or $C_4$-$C_{19}$ liquid hydrocarbons, respectively. These (i) decreases in selectivity to (and/or yield of) wax, and/or (ii) increases in selectivity to (and/or yield of) $C_4$-$C_{19}$ liquid hydrocarbons, as a result of incorporating the finishing stage (e.g., finishing reactor), can be achieved without a significant difference between the CO conversion obtained in the baseline FT synthesis stage and that obtained in the combined FT synthesis and finishing stages. For example, the CO conversion values obtained in both the baseline FT synthesis stage and combined FT synthesis and finishing stages may be within a range as described above with respect to the performance criteria of the FT synthesis stage. That is, the finishing stage typically does not significantly impact the CO conversion obtained in the FT synthesis stage alone, such that the CO conversion achieved in both the baseline FT synthesis stage and combined FT synthesis and finishing stages may be the same or substantially the same.

The conversion levels in the finishing stage, as described above, may be based on "per-pass" conversion, achieved in a single pass through the finishing stage (e.g., a finishing reactor of this stage), or otherwise based on overall conversion, achieved by returning a recycle portion of the finishing product back to the finishing stage (e.g., a finishing reactor of this stage), as described above with respect to the FT synthesis stage. A desired conversion of normal $C_{20}^+$ hydrocarbons may be achieved by adjusting the finishing reaction conditions described above (e.g., finishing reaction temperature and/or pressure), and/or adjusting the weight hourly space velocity (WHSV), as defined above. The finishing reaction conditions may include a weight hourly space velocity (WHSV) generally from about 0.05 $hr^{-1}$ to about 35 $hr^{-1}$, typically from about 0.1 $hr^{-1}$ to about 20 $hr^{-1}$, and often from about 0.5 $hr^{-1}$ to about 10 $hr^{-1}$. The finishing reaction conditions may optionally include returning a recycle portion of the finishing product, exiting the finishing reactor, back to the finishing feed for combining with the finishing feed, or otherwise back to the finishing reactor itself. Recycle operation allows for operation at relatively low "per-pass" conversion through the finishing reactor, while achieving a high overall conversion due to the recycle. Preferably, however, the finishing reaction conditions include little or even no finishing product recycle. For example, the finishing reaction conditions may include a weight ratio of recycled finishing product to finishing feed (i.e., a "recycle ratio"), with this recycled finishing product and finishing feed together providing a combined feed to the FT reactor, of those described above with respect to the FT synthesis stage. Preferably, the recycle ratio may be 0, meaning that no finishing product recycle is used, such that the per-pass conversion is equal to the overall conversion. Advantageously, in the absence of finishing product recycle, utility costs are saved and the overall design of the integrated process is simplified.

Embodiments of the invention are therefore directed to a process for converting $C_{20}^+$ hydrocarbons (e.g., normal $C_{20}^+$ hydrocarbons) in a feed comprising $C_4^+$ hydrocarbons, such as a finishing feed as described above, which may comprise all or a portion of an FT product as described above. The feed comprising $C_4^+$ hydrocarbons may comprise, for example, $C_{20}^+$ hydrocarbons in an amount of at least about 5 wt-% (e.g., from about 5 wt-% to about 30 wt-%), or at least about 10 wt-% (e.g., from about 10 wt-% to about 25 wt-%), based on the weight of total hydrocarbons, or based on the weight of the feed. The feed may further comprise hydrogen (e.g., in an amount as described above with respect to a finishing feed), CO, and/or $CO_2$. The process comprises contacting the feed with a finishing or dewaxing catalyst as described above, for example comprising an active metal selected from Groups 12-14 of the Periodic Table (e.g., gallium) on a zeolitic molecular sieve support (e.g., ZSM-5), to achieve conversion of the $C_{20}^+$ hydrocarbons at conversion levels, and with yields and selectivities to lower number hydrocarbons, and hydrocarbon fractions, as well as other performance criteria, as described herein.

Overall Performance Criteria, Advantages, and Exemplary Embodiments

An integrated process as described above, and particularly utilizing the combination of (i) a dry reforming or $CO_2$-steam reforming process as described above, in combination with (ii) Fischer-Tropsch synthesis, and (iii) optional finishing (dewaxing), may be referred to as an "integrated CSR-FT process," and used for the direct conversion of hydrocarbons such as methane in natural gas to one or more liquid fuels. Such liquid fuel(s) may be provided in a finishing product exiting the finishing stage (e.g., a reactor of this stage) as described above, together with low carbon number hydrocarbons, such as $C_1$-$C_3$ hydrocarbons. These low carbon number hydrocarbons, together with residual, unconverted gases (e.g., $H_2$, CO, and/or $CO_2$) may be separated from the liquid fuel(s) (e.g., comprising $C_4$-$C_{19}$ hydrocarbons and optionally branched $C_{20}^+$ hydrocarbons) using a flash separation vessel providing a vapor-liquid equilibrium separation stage. Alternatively, multiple vapor-liquid equilibrium separation stages may be used, as in the case of separation using distillation, to separate such low carbon number hydrocarbons and also separate the liquid fuels, for example by separating a fraction comprising predominantly, substantially all, or all, gasoline boiling-range hydrocarbons from a fraction comprising predominantly, substantially all, or all, diesel boiling-range hydrocarbons. In yet other embodiments, a flash separation vessel may be used to perform an initial separation of low carbon number hydrocarbons and residual gases from the finishing product, followed by separation of liquid fuels in the finishing product using distillation.

A number of advantages arise in integrated CSR-FT processes described herein, which include those associated with operation of the FT synthesis stage at a high per-pass conversion, as described above. These advantages include an option to operate the FT synthesis stage without recycle and with a shift in the distribution of hydrocarbons in the FT product toward those having higher numbers of carbon atoms and present in liquid fuels, thereby decreasing the yield of less desirable $C_1$-$C_3$ hydrocarbons. In representative embodiments, integrated CSR-FT processes can convert hydrocarbons (e.g., methane) present in a gaseous mixture and/or hydrocarbon-containing feedstock as described above and fed to the process, such that at least about 70% (e.g., from about 70% to about 95%), or at least about 85% (e.g., from about 85% to about 95%) of the carbon, initially present in hydrocarbons converted in the process, is present in $C_4$-$C_{19}$ liquid hydrocarbons in the finishing product. That is, the selectivity of the overall integrated CSR-FT process to liquid fuel(s) comprising these hydrocarbons (e.g., naphtha boiling-range hydrocarbons and diesel boiling-range hydrocarbons) may be in these ranges. Also, at most about 25% (e.g., from about 5% to about 25%), or at most about 15% (e.g., from about 10% to about 15%) of the carbon, initially present in hydrocarbons converted in the process, may be present in $C_1$-$C_3$ hydrocarbons in the finishing product. That is, the selectivity of the overall integrated CSR-FT process to these low carbon number hydrocarbons may be in these ranges. In addition, to the extent that these low carbon number hydrocarbons may be separated as a vapor fraction of the finishing product, this vapor fraction, due to its combustive heating (fuel) value, may be combusted to provide heat energy elsewhere in the integrated CSR-FT process, particularly in the furnace or hotbox of a reforming reactor of the reforming stage. This would allow for the generation of at least a portion, and possibly all, of the heat needed to sustain the endothermic dry reforming and/or $CO_2$-steam reforming reactions of the reforming stage, particularly in view of the fact that the vapor fraction typically comprises not only $C_1$-$C_3$ hydrocarbons, but also residual $H_2$ and/or CO that are likewise combustible.

Moreover, the use of the optional finishing stage can effectively convert all or substantially all wax (e.g., comprising normal $C_{20}^+$ hydrocarbons) to hydrocarbons having lower carbon numbers (e.g., within the range of $C_4$-$C_{19}$ hydrocarbons) and useful as liquid fuels. The optional finishing stage can also convert a portion of the wax to isoparaffinic $C_{20}^+$ hydrocarbons having a melting point below room temperature. To the extent that any hydrocarbons having a melting point above room temperature are present in the finishing product, the amount of such hydrocarbons may be sufficiently small so as to be completely soluble in this product, thereby beneficially rendering a liquid fraction of the finishing product suitable for transport via pipeline. Furthermore, the finishing stage can isomerize other hydrocarbons (e.g., $C_4$-$C_{19}$ hydrocarbons) present in the FT product and/or finishing feed, thereby increasing the octane number of gasoline boiling-range hydrocarbons and/or decreasing the pour point and/or cloud point of diesel boiling-range hydrocarbons present in the finishing product, relative to the respective values in the FT product and/or finishing feed.

Figure 3:
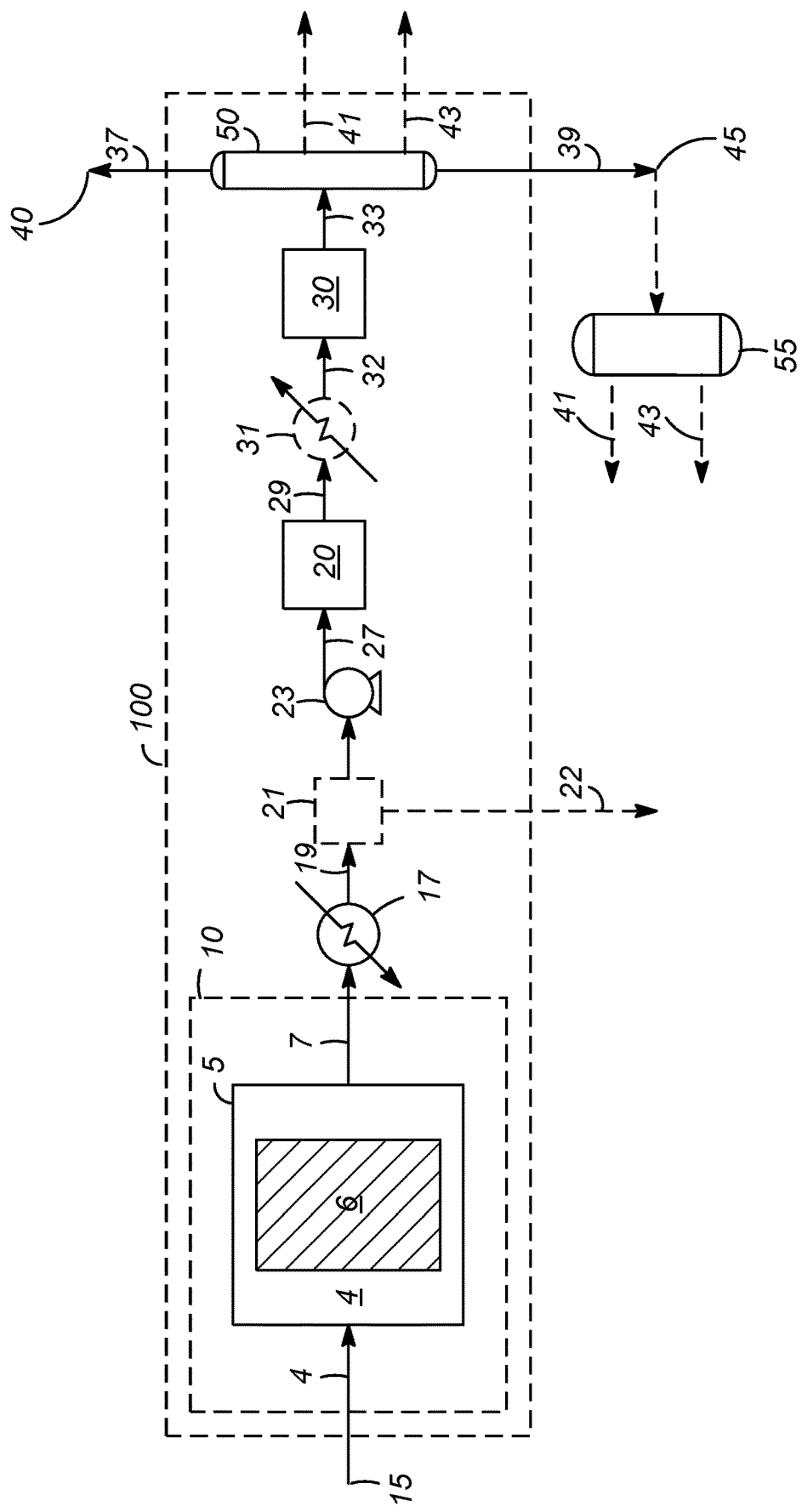
FIG. 3 depicts a flowscheme in which a dry reforming or CO₂-steam reforming process, such as depicted in FIG. 1A or 1i, is integrated with downstream processing steps for producing liquid hydrocarbons.

FIG. 3 depicts a flowscheme of a representative, integrated CSR-FT process 100, in which a dry reforming or $CO_2$-steam reforming process 10, such as described above and depicted in FIG. 1A or 1i, is integrated with downstream processing steps using FT reactor 20 and finishing reactor 30, for producing liquid hydrocarbons as described above. According to integrated CSR-FT process 100, gaseous mixture 4 may be provided via a connection, such as from system input 15, to a source of the gaseous mixture or a source of one or more components of this gaseous mixture (e.g., a hydrocarbon-containing feedstock such as natural gas), as described above. From system input 15, gaseous mixture 4 may be directed to reforming reactor 5, which may operate under reforming conditions as described above and may optionally comprise reforming catalyst 6, such as a catalyst as described above. Synthesis gas product 7, received from reforming reactor 5, may be directed to synthesis gas product cooler 17 and cooled, for example, from a temperature representative of a reforming condition as described above, to a temperature representative of a downstream FT reaction condition as described above. Cooled synthesis gas product 19 may be received from synthesis gas product cooler 17 and directed to optional condenser 21, for the removal of condensed water 22 from cooled synthesis gas product 19. Condensed water 22 in this case may be provided as a system water (or aqueous product) output.

Whether or not optional condenser 21 is included or excluded from integrated CSR-FT process 100, cooled synthesis gas product 19 may be directed to compressor 23 to increase the pressure of cooled synthesis gas product 19 to a pressure representative of an FT reaction condition as described above. FT feed 27 may be received from compressor 23 and directed to FT reactor 20, which may operate under FT reaction conditions as described above and may optionally comprise an FT catalyst as described above. Therefore, all or part of synthesis gas product 7 may be directed to FT reactor 20, to form all or part of FT feed 27 (e.g., a part of synthesis gas product 7, obtained after condensing water, may form all, or substantially all, of FT feed 27). FT product 29 may be received from FT reactor 20 and directed to optional FT product heater 31. Optional FT product heater 31 may be used to heat FT product 29 to a temperature representative of a finishing reaction condition as described above. Alternatively, both FT reactor 20 and downstream finishing reactor 30 may be operated at the same or substantially the same temperature, such that optional FT product heater 31 may be excluded from integrated CSR-FT process 100. All or part of FT product 29 may be directed to finishing reactor 30, to form all or part of finishing feed 32 (e.g., all of FT product 29 may form all, or substantially all, of finishing feed 32). Finishing reactor 30 may operate under finishing reaction conditions as described above and may optionally comprise a finishing catalyst as described above. Finishing product 33 may be received from finishing reactor 30 and directed to finishing product separator 50 that provides separated fractions of finishing product 33, such as vapor fraction 37 and liquid fraction 39, to a system vapor output 40 and to a system liquid output 45, respectively.

According to alternative embodiments, vapor fraction 37, received from finishing product separator 50, may be maintained within integrated CSR-FT process 100 and directed to a furnace or hotbox of reforming reactor 5, as a source of fuel to maintain reforming catalyst 6 at a temperature representative of a reforming condition as described above. In such embodiments, a flue gas effluent (not shown) may be provided as a system vapor output, in lieu of vapor fraction 37. According to other alternative embodiments, in addition to vapor fraction 37 (which may alternatively be used as a fuel source for heating reforming reactor 5 as described above), separator 50 may provide more defined liquid fractions of finishing product, such as gasoline boiling-range hydrocarbon containing fraction 41 and diesel boiling-range hydrocarbon containing fraction 43 as system liquid outputs, for example in the case of separator 50 operating as a distillation column to resolve these fractions, as opposed to a single stage (vapor/liquid) flash separator. In this case, liquid fraction 39 may be, more particularly, a high carbon number hydrocarbon containing fraction, such as a VGO boiling-range containing hydrocarbon fraction. According to further embodiments, separator 50 may provide all or substantially all of liquid fraction 39 of finishing product 33 to secondary separator 55 to provide more defined liquid fractions 41, 43 as described above with respect to separator 50. In this case, as depicted in FIG. 3, secondary separator 55 may be outside of integrated CSR-FT process 100 (e.g., may be used at a remote site to resolve liquid fractions), or otherwise may be included within this process.

Aspects of the invention, in addition to integrated CSR-FT processes, therefore also relate to systems or apparatuses for performing such processes, including integrated CSR-FT process 100 as depicted in FIG. 3. Accordingly, particular embodiments of the invention are directed to systems or apparatuses for producing $C_4^+$ hydrocarbons, useful as liquid fuels, from methane and/or other light hydrocarbons. The systems or apparatuses may comprise one or more of the following: (i) a reforming reactor 5 configured to connect, via a system input 15, to a source of a gaseous mixture 4, for example a source of natural gas comprising methane and $CO_2$. The reforming reactor 5 may contain a reforming catalyst 4 as described above and/or may be further configured to produce or provide, from the gaseous mixture 4, a synthesis gas product 7 comprising $H_2$ and CO, for example under reforming conditions as described above; (ii) a synthesis gas product cooler 17 configured to receive (and/or cool) the synthesis gas product 7 from the reforming reactor 5. The synthesis gas product cooler 17 may be connected to the reforming reactor 5, or may otherwise have an inlet configured for connection to an outlet of the reforming reactor 5; (iii) a compressor 23 configured to receive (and/or compress) a cooled synthesis gas product 19 from the synthesis gas product cooler 17. The compressor 23 may be connected to the synthesis gas product cooler 17, or may otherwise have an inlet configured for connection to an outlet of the synthesis gas product cooler 17; (iv) an FT reactor 20 configured to receive an FT feed 27 (e.g., as a compressed output) from the compressor 23. The FT reactor 20 may contain an FT catalyst as described above and/or may be further configured produce or provide, from the FT feed 27, an FT product 29 comprising hydrocarbons, including $C_4^+$ hydrocarbons, by conversion of the $H_2$ and CO in the synthesis gas product 7, for example under FT reaction conditions as described above. The FT reactor 20 may be connected to the compressor 23, or may otherwise have an inlet configured for connection to an outlet of the compressor 23; (v) a finishing reactor 30 configured to receive a finishing feed 32, either as a heated output from an optional FT product heater 31, or otherwise directly as FT product 29. The finishing reactor 30 may contain a finishing catalyst as described above and/or may be further configured to produce or provide a finishing product 33 comprising normal and branched $C_4$-$C_{19}$ hydrocarbons, by conversion of normal $C_{20}^+$ hydrocarbons in the FT product 29, for example under finishing reaction conditions as described above. The finishing reactor 30 may be connected to either the FT reactor 20 or the optional FT product heater 31, or the finishing reactor 30 may have an inlet configured for connection to an outlet of either the FT reactor 20 or the optional FT product heater 31; and (vi) a finishing product separator 50 configured to receive the finishing product 33 from the finishing reactor 30 and further configured to provide or separate, via a system vapor output 40 and a system liquid output 45, vapor and liquid fractions 37, 39, respectively, of the finishing product 33. The finishing product separator 50 may be connected to the finishing reactor 33 or may have an inlet configured for connection to an outlet of the finishing reactor 33. The separator 50 may otherwise be configured to provide more defined liquid fractions 41, 43 of the finishing product 33, as described above, as system liquid outputs. The separator 50 may alternatively be connected, or configured for connection, to secondary separator 55 to provide more defined liquid fractions 41, 43, as described above.

Integrated CSR-FT process 100, or associated system or apparatus, may optionally further comprise a condenser 21 configured to condense liquid water from the cooled synthesis gas product 19. In this case, the compressor 23 is configured to receive the cooled synthesis gas product 19 from the condenser 21, following the removal of condensed water 22, which may be provided as a system water (or aqueous product) output. The compressor 23 may be connected to the condenser 21, or may otherwise have an inlet configured for connection to an outlet of the condenser 21.

In view of the above description, it can be appreciated that integrated CSR-FT processes, as well as associated systems and apparatuses, can provide a highly economical manner of converting hydrocarbon-containing gases such as methane to liquid fuels. Each process step, or each system element, can be seamlessly integrated with the next step or element. Such integration is possible, advantageously, without the need for certain conventional steps and associated elements (equipment) and costs (both capital and operating), such as by the omission of one or more of the following steps: (i) removal of $CO_2$ (e.g., using amine scrubbing) from a source of natural gas with a high $CO_2$ content, (ii) adjustment of the molar $H_2$:CO ratio of the synthesis gas product, upstream of the FT reactor, (iii) separation of solid or condensed liquid wax (e.g., comprising normal $C_{20}^+$ hydrocarbons) from the FT product, upstream of the finishing reactor (e.g., for processing of the solid wax in a separate hydrotreating reactor). In fact, CSR-FT processes, as well as associated systems and apparatuses, as described herein, can advantageously operate such that no materials are added and/or removed along the stages of reforming, FT synthesis, and finishing, except for the addition of gaseous mixture 4 and the removal of fractions of finishing product 33, with the possibility also of removing condensed water 22 (or aqueous product). In this manner, integrated CSR-FT processes, and associated systems and apparatuses, may be streamlined and simplified, allowing for their operation and implementation with favorable economics associated with liquid fuel production.

Moreover, this simplicity allows such integrated CSR-FT processes, and associated systems and apparatuses, to be operable on a small scale and even transportable in some embodiments, for example by truck, ship, train, or plane. For example, integrated CSR-FT process 100, or the associated system or apparatus as described above, may be mounted on a skid (skid-mounted) for ease of transport to sources of natural gas, sources of other suitable hydrocarbon-containing feedstocks, and/or even sources of $CO_2$-containing industrial waste gases. For example, integrated CSR-FT process 100 may advantageously be used for converting flared natural gas to liquid fuels and reducing greenhouse gas (GHG) emissions at well sites. In the case of such a process being transportable, a single process, or its associated system or apparatus, could be used for both of these purposes, and/or used with a variety of other different gaseous mixtures and components of these mixtures (e.g., hydrocarbon-containing feedstocks), as described above, even if their sources are at different locations.

Integration with Biomass Hydropyrolysis

As described above, processes for producing renewable hydrocarbon fuels from the hydropyrolysis of biomass can provide gaseous mixtures comprising methane and/or other light hydrocarbons, in combination with $CO_2$. Therefore, such gaseous mixtures represent potential feeds to $CO_2$-steam reforming processes, or otherwise integrated CSR-FT processes, as described above, which can be converted to (i) a hydrogen-containing synthesis gas, in the case of a $CO_2$-steam reforming process, or (ii) liquid fuels, in the case of an integrated CSR-FT process. With respect to embodiment (i), the hydrogen-containing synthesis gas can be used, optionally following purification to obtain an $H_2$-enriched portion thereof, as a source of hydrogen that is used to sustain the hydropyrolysis process. With respect to embodiment (ii), the liquid fuels produced from the integrated CSR-FT process can beneficially increase the overall yield of biogenic (renewable) liquid fuels, relative to the yield that may otherwise be obtained from biomass hydropyrolysis. This increase may be relative to a baseline yield in the absence of using any reaction stage of an integrated CSR-FT process, which corresponds also to the baseline yield obtained using the reforming stage to produce a synthesis gas product, but in the absence of converting the $H_2$ and CO in the synthesis gas product to hydrocarbons using an FT synthesis stage, as described above. According to some embodiments, the increase in the yield of biogenic liquid fuels may be at least about 25% (e.g., from about 25% to about 60%), or at least about 35% (e.g., from about 35% to about 50%).

Figure 4:
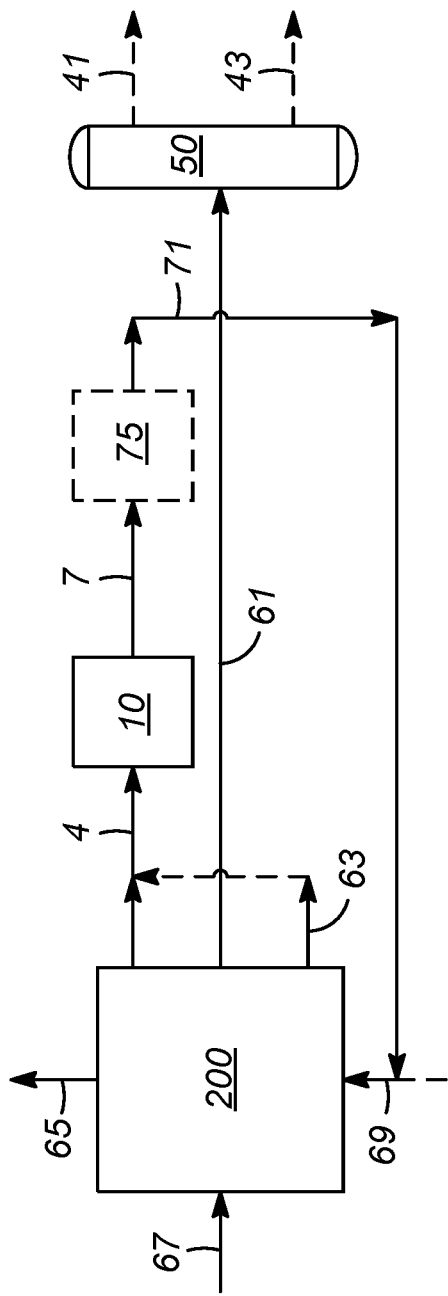
FIG. 4 depicts a flowscheme in which a dry reforming or CO₂-steam reforming process, such as depicted in FIG. 1A or 1B, is used with a process for producing a renewable hydrocarbon fuel from the hydropyrolysis of biomass.

FIG. 4 depicts a flowscheme in which hydropyrolysis process 200 generates gaseous mixture 4, comprising methane and $CO_2$, as a feed to a $CO_2$-steam reforming process 10, such as depicted in FIG. 1A or FIG. 1B. According to this embodiment, therefore, $CO_2$-steam reforming process 10 is integrated with a process for producing a renewable hydrocarbon fuel from the hydropyrolysis of biomass. Gaseous mixture 4 may comprise methane and $CO_2$, as well as other species, in concentrations as described above with respect to "a hydropyrolysis gaseous mixture." In addition to gaseous mixture 4, hydropyrolysis process 200 also generates substantially fully deoxygenated hydrocarbon liquid 61 (e.g., having a total oxygen content of less than about 2 wt-% or less than about 1 wt-%), comprising hydrocarbons that may be separated into gasoline boiling-range hydrocarbon containing fraction 41 and diesel boiling-range hydrocarbon containing fraction 43. Hydropyrolysis process 200 may further generate aqueous liquid 63, for example obtained by phase separation from substantially fully deoxygenated hydrocarbon liquid 61. As shown, all or a portion of aqueous liquid 63 may optionally be combined with gaseous mixture 4, for example to adjust the molar $H_2O:CO_2$ ratio of gaseous mixture 4 to $CO_2$-steam reforming process 10, to molar ratios as described above. Hydropyrolysis process 200 may further generate solid char 65. These products of hydropyrolysis process 200, including gaseous mixture 4, substantially fully deoxygenated hydrocarbon liquid 61, and aqueous liquid 63 are generated from feeds to hydropyrolysis process 200, including biomass-containing or biomass-derived feedstock 67 and hydrogen-containing feed gas stream 69.

With respect to biomass-containing or biomass-derived feedstock 67, the term "biomass" refers to substances derived from organisms living above the earth's surface or within the earth's oceans, rivers, and/or lakes. Representative biomass can include any plant material, or mixture of plant materials, such as a hardwood (e.g., whitewood), a softwood, a hardwood or softwood bark, lignin, algae, and/or lemna (sea weeds). Energy crops, or otherwise agricultural residues (e.g., logging residues) or other types of plant wastes or plant-derived wastes, may also be used as plant materials. Specific exemplary plant materials include corn fiber, corn stover, and sugar cane bagasse, in addition to "on-purpose" energy crops such as switchgrass, miscanthus, and algae. Short rotation forestry products, such as energy crops, include alder, ash, southern beech, birch, eucalyptus, poplar, willow, paper mulberry, Australian Blackwood, sycamore, and varieties of paulownia elongate. Other examples of suitable biomass include vegetable oils, carbohydrates (e.g., sugars), organic waste materials, such as waste paper, construction, demolition wastes, and biosludge.

A "biomass-containing" feedstock may comprise all or substantially all biomass, but may also contain non-biological materials (e.g., materials derived from petroleum, such as plastics, or materials derived from minerals extracted from the earth, such as metals and metal oxides, including glass). An example of a "biomass-containing" feedstock that may comprise one or more non-biological materials is municipal solid waste (MSW).

"Biomass-derived," for example when used in the phrase "biomass-derived feedstock," refers to products resulting or obtained from the thermal and/or chemical transformation of biomass, as defined above, or biomass-containing feedstocks (e.g., MSW). Representative biomass-derived feedstocks therefore include, but are not limited to, products of pyrolysis (e.g., bio-oils), torrefaction (e.g., torrefied and optionally densified wood), hydrothermal carbonization (e.g., biomass that is pretreated and densified by acid hydrolysis in hot, compressed water), and polymerization (e.g., organic polymers derived from plant monomers). Other specific examples of biomass-derived products (e.g., for use as feedstocks) include black liquor, pure lignin, and lignin sulfonate. Biomass-derived feedstocks also extend to pretreated feedstocks that result or are obtained from thermal and/or chemical transformation, prior to, or upstream of, their use as feedstocks for a given conversion step (e.g., hydropyrolysis). Specific types of pretreating steps that result in biomass-derived products include those involving devolatilization and/or at least some hydropyrolysis of a biomass-containing feedstock. Therefore, certain pretreated feedstocks are also "biomass-derived" feedstocks, whereas other pretreated feedstocks, for example resulting or obtained from classification without thermal or chemical transformation, are "biomass-containing" feedstocks, but not "biomass-derived" feedstocks.

It is therefore also possible to feed to hydropyrolysis process 200, in place of all or a portion of the biomass-containing feedstock, a biomass-derived feedstock, such as a pretreated feedstock that is obtained from a biomass-containing feedstock, after having been devolatilized and/or partially hydropyrolyzed in a pretreating reactor (pre-reactor), upstream of a hydropyrolysis reactor vessel. Such pre-reactor thermal and/or chemical transformations of biomass may be accompanied by other, supplemental transformations, for example to reduce corrosive species content, reduce hydropyrolysis catalyst poison content (e.g., reduced sodium), and/or a reduce hydroconversion catalyst poison content. Devolatilization and/or partial hydropyrolysis of biomass or a biomass-containing feedstock in a pre-reactor may be carried out in the presence of a suitable solid bed material, for example a pretreating catalyst, a sorbent, a heat transfer medium, and mixtures thereof, to aid in effecting such supplemental transformations and thereby improve the quality of the pretreated feedstock. Suitable solid bed materials include those having dual or multiple functions. In the case of a pretreating catalyst, those having activity for hydroprocessing of the biomass-containing feedstock, described below, are representative.

It is also possible to feed a biomass-containing feedstock that is a pretreated feedstock, obtained after having been subjected to a pretreating step, for example a physical classification to improve at least one characteristic, such as a reduced non-biological material content (e.g., content of glass, metals, and metallic oxides, including all mineral forms), a reduced average particle size, a reduced average particle aerodynamic diameter, an increased average particle surface area to mass ratio, or a more uniform particle size.

$CO_2$-steam reforming process 10, as depicted in FIG. 4, may include a reforming reactor 5, containing a reforming catalyst 6, as depicted in FIG. 1A or 1, with this catalyst having a composition as described above. Reforming reactor 5 may operate under reforming conditions as described above, to produce synthesis gas product 7 comprising $H_2$ and CO. Optional hydrogen purification module 75, for example utilizing pressure-swing adsorption (PSA) or membrane separation, may be used to obtain $H_2$-enriched portion 71 of synthesis gas product 7, having a higher concentration of hydrogen relative to this product (e.g., having a hydrogen concentration of at least about 80 mol-%, such as from about 80 mol-% to about 99 mol-%, or at least about 85 mol-%, such as from about 85 mol-% to about 98 mol-%). As shown in FIG. 4, $H_2$-enriched portion 71 may be directed back to hydropyrolysis process 200, to provide at least a portion, and possibly all, of hydrogen-containing feed gas stream 69. An $H_2$-depleted portion of synthesis gas product (not shown) may also be obtained from hydrogen purification module 75 and possibly combusted to provide heat energy for $CO_2$-steam reforming process 10 or for hydropyrolysis process 200. Hydrogen purification module 75 may be used to preferentially separate, into the $H_2$-depleted portion, any of CO, $CO_2$, light ($C_1$-$C_3$) hydrocarbons, and/or $H_2S$.

Figure 5:
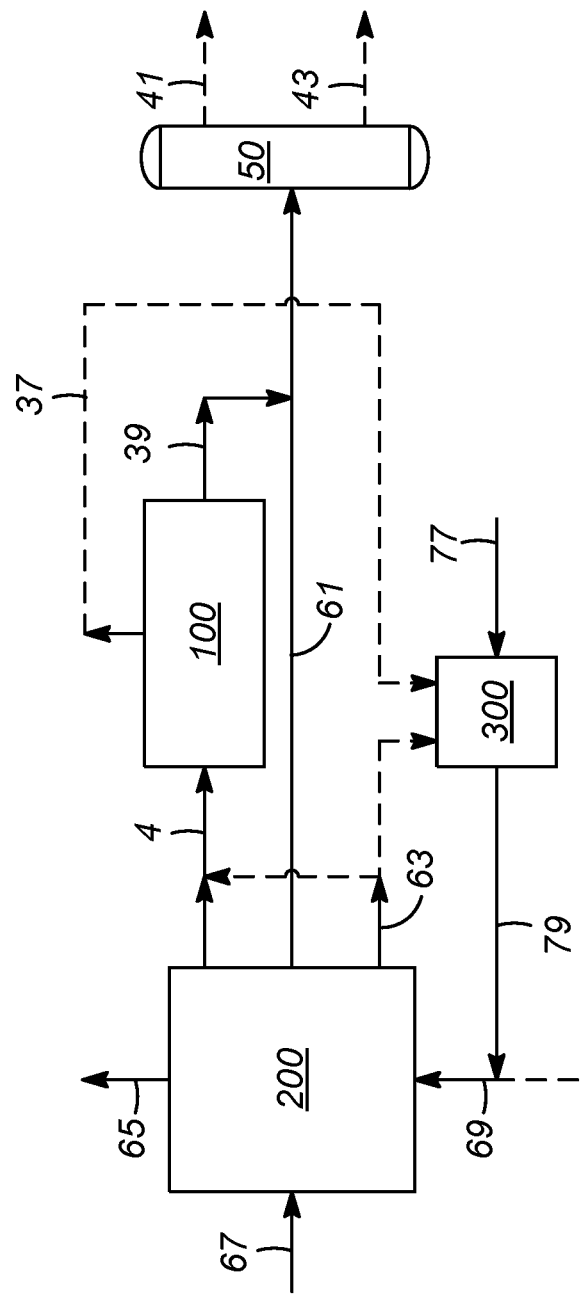
FIG. 5 depicts a flowscheme in which dry reforming or CO₂-steam reforming is integrated in an overall liquid hydrocarbon production process, such as depicted in FIG. 3, which is used with a process for producing a renewable hydrocarbon fuel from the hydropyrolysis of biomass.

FIG. 5 depicts a flowscheme in which hydropyrolysis process 200 generates gaseous mixture 4, comprising methane and $CO_2$, as in FIG. 4. According to the embodiment in FIG. 5, however, gaseous mixture 4 is a feed to integrated CSR-FT process 100, such as depicted in FIG. 3. therefore, integrated CSR-FT process 100 is in this case further integrated with a process for producing a renewable hydrocarbon fuel from the hydropyrolysis of biomass. Products generated from hydropyrolysis process 200 are as described above with respect to the embodiment of FIG. 4. These products include (i) gaseous mixture 4, (ii) substantially fully deoxygenated hydrocarbon liquid 61, comprising hydrocarbons that may be separated into gasoline boiling-range hydrocarbon containing fraction 41 and diesel boiling-range hydrocarbon containing fraction 43, (iii) aqueous liquid 63, and (iv) solid char 65. As also described above with respect to the embodiment of FIG. 4, all or a portion of aqueous liquid 63 may optionally be combined with gaseous mixture 4, for example to adjust the molar $H_2O$:$CO_2$ ratio of gaseous mixture 4. Because integrated CSR-FT process 100, to which gaseous mixture is directed in the embodiment of FIG. 5, includes an FT synthesis stage and optionally the use of an FT catalyst that is susceptible to sulfur poisoning, it may be preferable, according to some embodiments, to treat gaseous mixture 4 to remove $H_2S$ and/or other sulfur-bearing contaminants, prior to (upstream of) integrated CSR-FT process 100.

In the embodiment of FIG. 5, integrated CSR-FT process 100 provides liquid fraction 39 of finishing product 33, as described above with respect to FIG. 3. Liquid fraction 39 may advantageously comprise a gasoline boiling-range hydrocarbon containing fraction and/or a diesel boiling-range hydrocarbon containing fraction, either or both of which may increase the yields of these fractions 41, 43 relative to yields obtained from hydropyrolysis process 200 alone (baseline yields obtained in the absence of integrated CSR-FT process 100), for example according to the yield increases described herein. Also according to the embodiment of FIG. 5, vapor fraction 37 of finishing product 33 (FIG. 3), comprising methane and/or other light hydrocarbons (e.g., $C_2$-$C_3$ hydrocarbons), in addition to other combustible species such as residual $H_2$ and/or CO, may optionally be combusted as a source of fuel. As depicted in FIG. 5, a hydrogen production process 300 as described above is used to generate purified hydrogen product 79 by steam methane reforming (SMR) of natural gas 77 supplied to this process. Vapor fraction 37 may therefore be used to generate heat for SMR, as depicted in FIG. 5, and all or a portion of aqueous liquid 63 from hydropyrolysis process 200 may be used to generate steam for SMR used in hydrogen production process 300. Purified hydrogen product 79 may be used to provide all or a portion of hydrogen-containing feed gas stream 69 to hydropyrolysis process 200.

Figure 6:
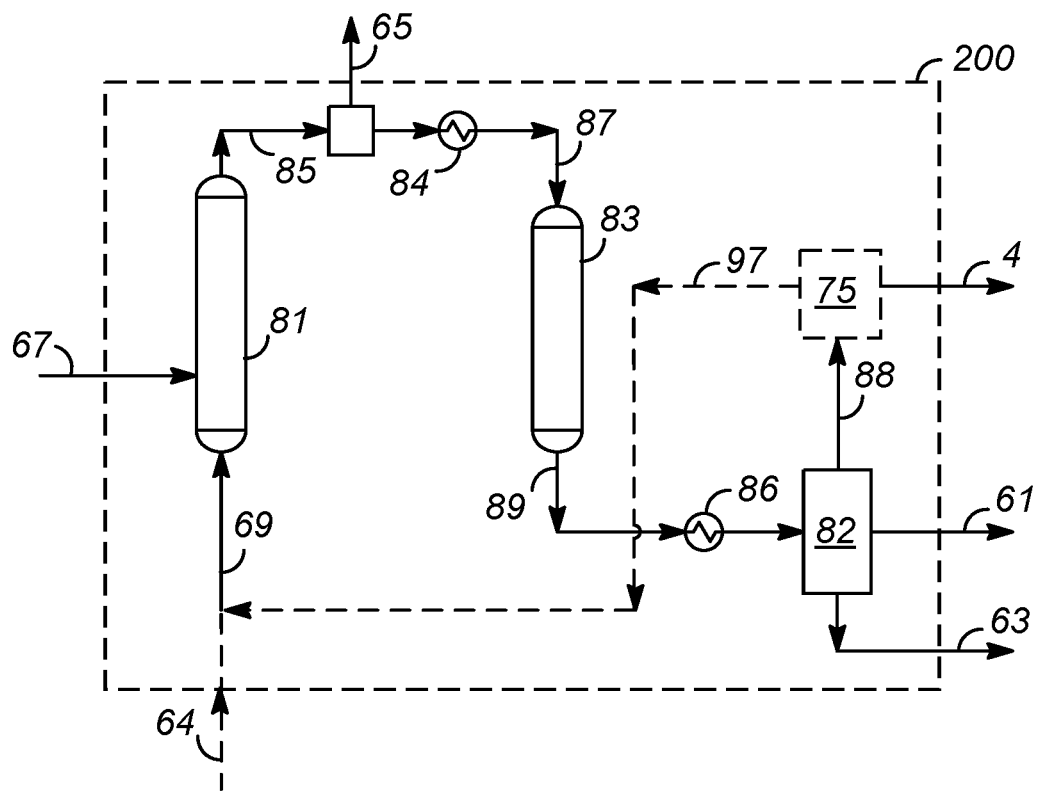
FIG. 6 depicts a flowscheme of a process for producing a renewable hydrocarbon fuel from the hydropyrolysis of biomass, such as a process with which a dry reforming or CO₂-steam reforming process may be used, as depicted in FIG. 4, or with which an overall liquid hydrocarbon production process may be integrated, as depicted in FIG. 5.

FIG. 6 provides additional details of a hydropyrolysis process 200, for example as depicted in FIGS. 4 and 5 and used to convert biomass-containing or biomass-derived feedstock 67 and hydrogen-containing feed gas stream 69 to provide (i) gaseous mixture 4 comprising methane and $CO_2$, (ii) substantially fully deoxygenated hydrocarbon liquid 61 comprising liquid hydrocarbon-containing fractions, (iii) aqueous liquid 63, and (iv) solid char 65. As depicted in FIG. 6, hydropyrolysis process 200 may include two stages of reaction, carried out in first stage hydropyrolysis reactor 81 and second stage hydroconversion reactor 83. Hydropyrolysis reactor 81 may operate as a catalytic fluidized bed reactor to devolatilize feedstock 67 in the presence of stabilizing hydrogen, producing hydropyrolysis reactor effluent 85. Following the removal of solid char 65 from hydropyrolysis reactor effluent 85 and cooling in first stage effluent cooler 84, hydropyrolysis vapors 87, including a partially deoxygenated hydropyrolysis product, light hydrocarbons, $H_2$, CO, $CO_2$, and $H_2O$, are directed to hydroconversion reactor 83. This reactor may operate as a fixed bed, for further catalytic hydrodeoxygenation of the partially deoxygenated hydropyrolysis product. Hydroconversion reactor effluent 89 is then directed to second stage effluent cooler 86, which condenses substantially fully deoxygenated hydrocarbon liquid 61 and aqueous liquid 63 from hydroconversion reactor effluent 89. In separator 82, these liquid products 61, 63 of hydropyrolysis process 200 may be separated by organic/aqueous phase separation, with the less dense phase, substantially fully deoxygenated hydrocarbon liquid 61, settling above the more dense phase, aqueous liquid 63.

Also in separator 82, product vapor fraction 88, comprising light hydrocarbons, $H_2$, CO, $CO_2$, and $H_2O$, may be separated by vapor/liquid phase separation. Product vapor fraction 88 may be sent to hydrogen purification module 75, for example utilizing pressure-swing adsorption (PSA) or membrane separation, to separate recycle hydrogen 97, having a higher concentration of hydrogen relative to product vapor fraction 88, from gaseous mixture 4. Gaseous mixture 4 may therefore have a lower concentration of hydrogen relative to product vapor fraction 88, and may have other composition characteristics as described above with respect to representative gaseous mixtures generally, and/or with respect to "a hydropyrolysis gaseous mixture" in particular.

Hydrogen purification module 75 may be used to preferentially separate, into gaseous mixture 4, any or all of light ($C_1$-$C_3$) hydrocarbons, CO, $CO_2$, $H_2O$, and/or $H_2S$. Recycle hydrogen 97 may have a hydrogen concentration, for example, of at least about 80 mol %, such as from about 80 mol-% to about 99 mol-%, or at least about 85 mol-%, such as from about 85 mol-% to about 98 mol-%. Recycle hydrogen 97 may be used to provide at least a portion, and possibly all, of hydrogen-containing feed gas stream 69. Optionally, external make-up hydrogen or fresh hydrogen 64 may be combined with recycle hydrogen 97 to provide hydrogen-containing feed gas stream 69.

Figure 7:
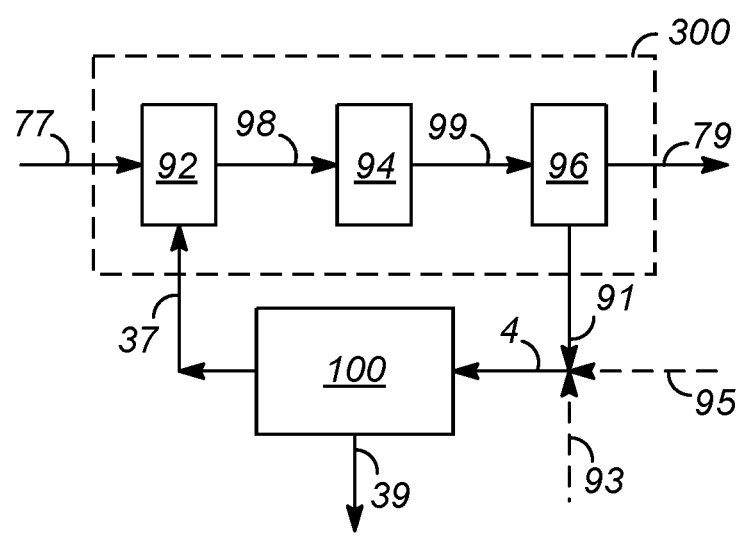
FIG. 7 depicts a flowscheme in which dry reforming or CO₂-steam reforming is integrated in an overall liquid hydrocarbon production process, such as illustrated in FIG. 3, which is used in a hydrogen production process.

FIG. 7 provides additional details of a hydrogen production process 300, for example as depicted in FIG. 5. As described above, a hydrogen production process may convert natural gas 77 to purified hydrogen product 79 using stages of steam methane reforming (SMR) 92, water-gas shift (WGS) reaction 94, and pressure-swing adsorption (PSA) 96. In this case, SMR can be used to generate SMR synthesis gas 98, and its hydrogen content can be increased with WGS reaction 94 to provide WGS product 99. PSA 96 is then used to recover purified hydrogen product 79 and reject non-hydrogen impurities (e.g., substantially all non-hydrogen impurities) in hydrogen-depleted PSA tail gas 91. Hydrogen-depleted PSA tail gas 91 generally comprises (i) unconverted methane (due to methane "breakthrough" from SMR 92), (ii) hydrogen that is not recovered in purified hydrogen product 79 using PSA 96, and (iii) $CO_2$, as well as typically CO and $H_2O$. Hydrogen-depleted PSA tail gas 91 may have other composition characteristics as described above with respect to gaseous mixtures generally, and/or with respect to "hydrogen-depleted PSA tail gas."

Normally, hydrogen-depleted PSA tail gas 91 that is obtained as a byproduct from hydrogen production process is combusted to recover its fuel value. The energy of this combustion can serve as an important source of heat for the furnace or hotbox of SMR 92, as this step of hydrogen production process 300 operates endothermically and at high temperatures (e.g., as high as 950° C. (1742° F.) or higher). According to the process depicted in FIG. 7, however, hydrogen-depleted PSA tail gas 91 is directed first to integrated CSR-FT process 100, for example as depicted in FIG. 3 and described above. Depending on the composition of hydrogen-depleted PSA tail gas 91, supplemental hydrocarbon source 95 (e.g., natural gas) and/or supplemental steam source 93 may optionally be combined with hydrogen-depleted PSA tail gas 91 to provide gaseous mixture 4, having a suitable composition as described above. In this manner, methane and $CO_2$ from hydrogen-depleted PSA tail gas 91 may be converted in integrated CSR-FT process 100 to produce liquid fraction 39 of finishing product 33 (FIG. 3), comprising liquid hydrocarbons useful as fuels. Although the consumption of methane thereby reduces the combustive heating value of hydrogen-depleted PSA tail gas 91, the value of liquid fraction 39 produced outweighs this loss of combustive heating value, which may be replaced, for example using lower cost natural gas. For example, this natural gas, as a supplemental fuel gas (not shown) to the furnace or hotbox of SMR 92, may be combined with vapor fraction 37 of finishing product 33 (FIG. 3), as vapor fraction 37 itself can provide some of the heat needed to maintain SMR 92.

The following examples are set forth as representative of the present invention. These examples are not to be construed as limiting the scope of the invention as other equivalent embodiments will be apparent in view of the present disclosure and appended claims.

Example 1

$CO_2$-Steam Reforming Studies

Pilot plant scale experiments were performed in which gaseous mixtures were fed continuously to a $CO_2$-steam reforming reactor containing catalyst particles having a composition of 1 wt-% Pt and 1 wt-% Rh on a cerium oxide support. The performance of the system for $CO_2$-steam reforming was tested at conditions of 0.7 hr$^{-1}$ WHSV, 760° C. (1400° F.), and a gauge pressure ranging from 124 kPa (18 psig) to 172 kPa (25 psig). Two types of gaseous mixtures tested were (1) a composition containing methane, ethane, propane, and $CO_2$, in addition to $H_2O$, and simulating that obtained from the combined hydropyrolysis and hydroconversion of biomass ("Renewable Type"), and (2) a typical natural gas composition having a high level of $CO_2$ ("Natural Gas Type"). The renewable type composition provided an example of a methane-containing feedstock that is also a "hydropyrolysis gaseous mixture," as described above. The natural gas type composition provided an example of a methane-containing feedstock that is also a "natural gas comprising $CO_2$," to which steam, as an $H_2O$-containing oxidant, has been added, as described above. These gaseous mixtures (combined feeds), and the synthesis gas products obtained from these feeds, are summarized in Table 1 below.

TABLE 1

$CO_2$-steam Reforming of Differing Gaseous Mixtures

| | Renewable Type Combined Feed | Renewable Type Synthesis Gas Product | Natural Gas Type Combined Feed | Natural gas Type Synthesis Gas Product |
|---|---|---|---|---|
| methane, mol-% | 11.7 | 0.3 | 21.7 | .79 |
| ethane, mol-% | 5.8 | 0 | 5.8 | 0 |
| propane, mol-% | 5.8 | 0 | 1.4 | 0 |
| $CO_2$, mol-% | 23.4 | 10.6 | 29.0 | 8.2 |
| water, mol-% | 53.3 | 12.7 | 42.1 | 8.6 |
| $H_2$, mol-% | | 51.3 | | 51.9 |
| CO, mol-% | | 25.1 | | 30.4 |
| % methane conversion | | 96 | | 93 |
| % ethane conversion | | 100 | | 100 |
| % propane conversion | | 100 | | 100 |
| molar $H_2$:CO ratio | | 2.05 | | 1.71 |

Figure 8:
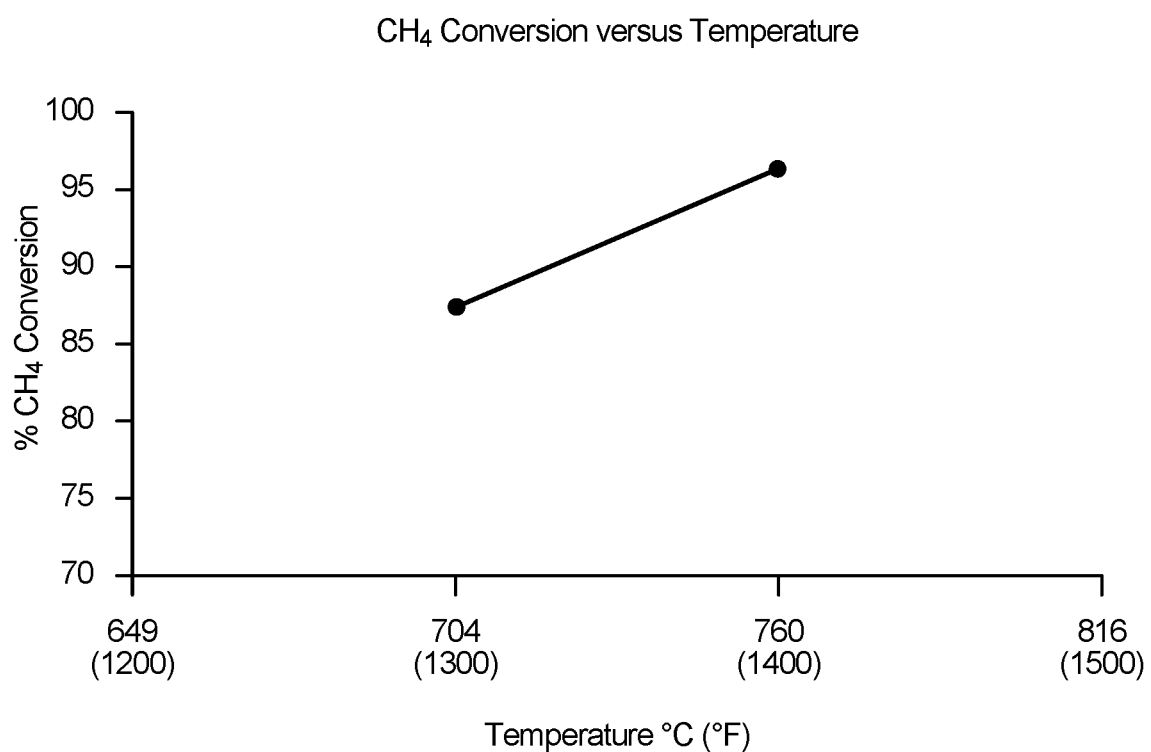
FIG. 8 illustrates the high activity, in terms of methane conversion, of reforming catalysts as described herein.
Figure 9:
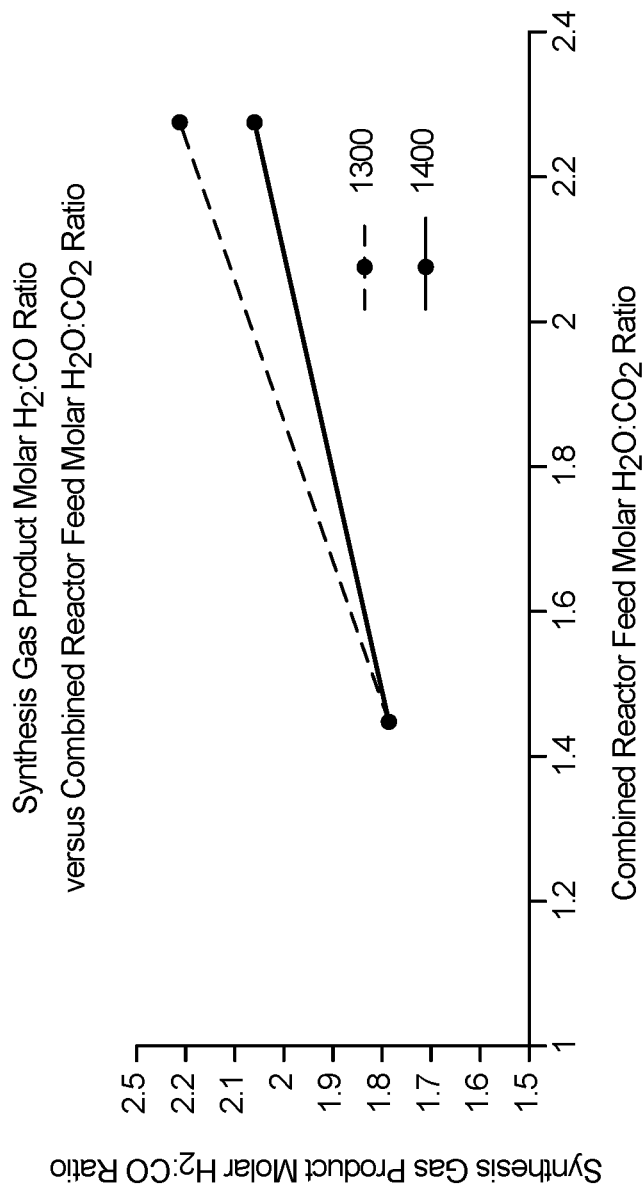
FIG. 9 illustrates the relationship between the molar H₂:CO ratio of the synthesis gas product and the molar H₂O/CO₂ ratio of the gaseous mixture in a CO₂-steam reforming reactor (as a combined feed) at different reaction temperatures, in the case of representative CO₂-steam reforming processes.

From these results, it can be seen that the $CO_2$-steam reforming catalyst and process can provide a synthesis gas product having a molar $H_2$:CO ratio that is nearly 2:1 and therefore suitable for subsequent, direct processing via the Fischer-Tropsch reaction, or at least without a prior (upstream) adjustment of this ratio. Whereas these favorable results were obtained at only 760° C. (1400° F.) reaction temperature, lower temperatures, such as 704° C. (1300° F.) are also possible, in view of the high activity of the catalyst. Lower operating temperatures tend to reduce the rate of side reactions that form coke, which deactivates the catalyst. FIG. 8 illustrates the relationship between temperature and methane conversion for feeds and reforming catalysts of the type tested in Example 1, and in particular this figure illustrates the ability to achieve greater than 85% methane conversion at 704° C. (1300° F.) and greater than 95% methane conversion at 760° C. (1400° F.). FIG. 9 illustrates how the molar $H_2O$:$CO_2$ ratio of the gaseous mixture, for feeds and reforming catalysts of the type tested in Example 1, influences the molar $H_2$:CO ratio of the synthesis gas product, at temperatures of both 704° C. (1300° F.) and 760° C. (1400° F.). In view of the possibility to establish relationships between these parameters for a given feed, reforming catalyst, and set of operating conditions, the gaseous mixture composition can serve as a convenient control for achieving a target synthesis gas product composition.

Example 2

Sulfur Tolerance of $CO_2$-Steam Reforming Catalysts

Additional experiments were conducted in which a typical natural gas composition as described in Example 1 was subjected to $CO_2$-steam reforming as also described in this example. However, the gaseous mixture or combined feed in this case was spiked with $H_2S$ at a concentration of 800 mol-ppm. Despite this high level of sulfur contamination, it was found that the offset in methane conversion was easily restored by increasing the reforming catalyst bed temperature from 760° C. (1400° F.) to 788° C. (1450° F.). Furthermore, the reforming catalyst surprisingly exhibited long-term stability over 400 operating hours (hours on stream) at this temperature, as well as the WHSV and pressure as described above with respect to Example 1. This stability, achieved despite the considerable sulfur concentration, was surprising in view of the sulfur sensitivity of conventional catalysts used for steam methane reforming.

Example 3

Long-Term $CO_2$-Steam Reforming Testing

Figure 10:
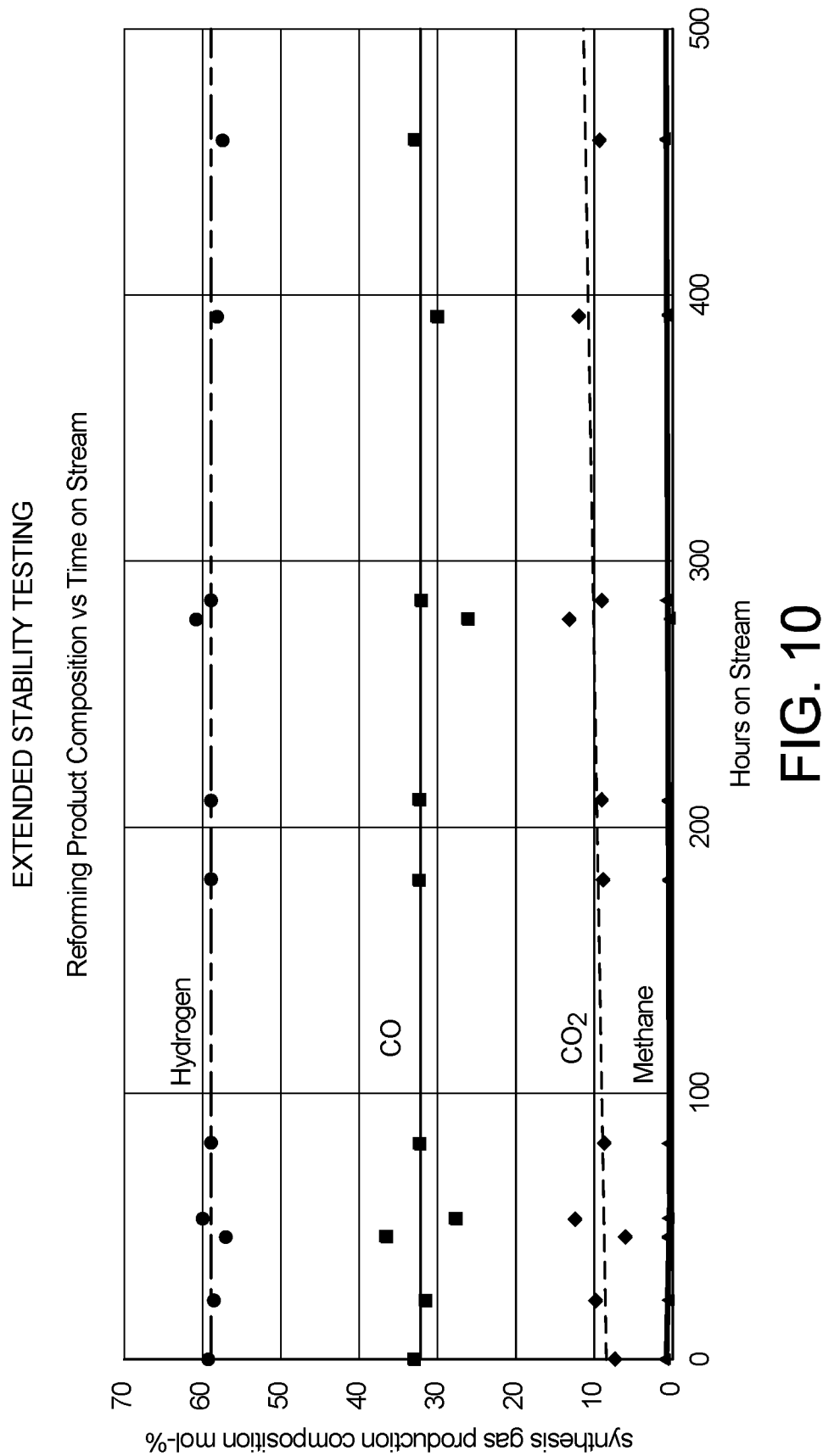
FIGS. 10 and 11 illustrate the long term operational stability of reforming catalysts as described herein, in a CO₂-steam reforming process over an extended operating period.
Figure 11:
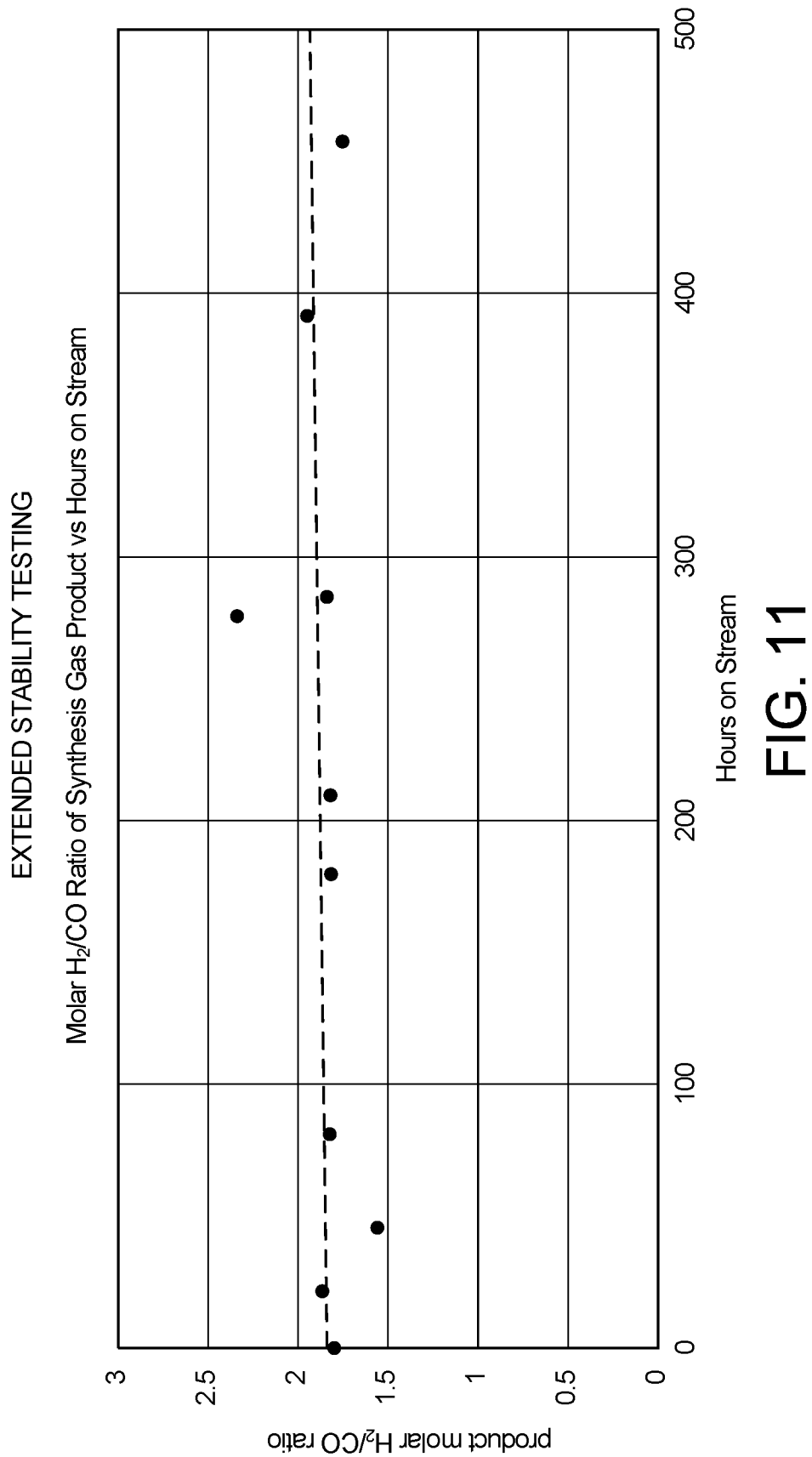

The gaseous mixture described in Example 1 as the "Renewable Type" and having the composition provided in Table 1 was tested using the catalyst and conditions as described in Example 1, to evaluate performance of the system for $CO_2$-steam reforming over an extended period of operation. The "Renewable Type" feed or gaseous mixture also provides an example of a representative "hydropyrolysis gaseous mixture" as described above. Long-term stability testing revealed that the composition of the synthesis gas product obtained was stable over 500 hours of operation under these constant conditions, demonstrating essentially no deactivation, over the extended operating period, of the reforming catalyst. FIG. 10 illustrates the stable synthesis gas product composition obtained over this operating period, with a high level of conversion of methane. FIG. 11 illustrates the stable molar $H_2$/CO ratio of the synthesis gas product obtained, which was nearly a ratio of 2 and therefore ideal for use in a downstream FT synthesis reaction to produce liquid hydrocarbons.

Example 4

Evaluation of the Hydroisomerization and Hydrocracking of Wax from FT Synthesis

The FT synthesis reaction typically produces hydrocarbons having a broad range of molecular weights (and carbon numbers), including normal $C_{20}^+$ hydrocarbons that are solid at room temperature and generally regarded as an undesirable wax product. The use of hydrocracking to eliminate this wax, by separating it from the FT product and converting it to lower number hydrocarbons, typically adds 1/3 of the capital cost to an FT synthesis complex, as well as a significant amount of complexity. Because it is a solid, wax is not easily shipped through pipelines nor blended with crude oil. With the objective of developing a simple integrated gas to liquid (GTL) process whereby wax produced in the FT synthesis reaction could be converted to, and thereby add to the yield of, (i) lower number hydrocarbons having value as liquid fuels, and/or (ii) isoparaffinic hydrocarbons having melting points below room temperature, a simple combined hydroisomerization/hydrocracking reaction for this purpose was studied. The use of hydroisomerization was considered as a potentially attractive alternative, as this reaction requires only small amounts of hydrogen. The incorporation of a step involving hydroisomerization directly after the FT synthesis stage, with this step being provided with all or substantially all of the FT product (e.g., without separation of wax) was therefore proposed as a low cost solution to the problem of wax production in this stage. This step, involving both hydroisomerization and hydrocracking of normal $C_{20}^+$ hydrocarbons, was referred to as the "finishing stage," utilizing at least one "finishing reactor."

In order to investigate possible catalysts for use in the hydroisomerization/hydrocracking of wax, $C_{23}$-$C_{60}$ straight chain paraffins were obtained from a commercial supplier of FT wax (Sasol). Batch experiments were performed by adding 200 grams of the wax to a stirred Parr bomb reactor. Following this addition of the wax, the temperature of the reactor was raised under flowing hydrogen or under a flowing synthesis gas (mixture of hydrogen and CO). The reactor, which had been loaded with 25 grams of finishing catalyst (or hydroisomerization/hydrocracking catalyst) absolute pressure was maintained at 2.76 MPa (400 psia). It was found that a catalyst formulation of 1 wt-% gallium on ZSM-5 zeolite support (Ga-ZSM-5 catalyst) was effective for converting the wax through hydroisomerization, combined with hydrocracking. These reactions in combination respectively resulted in the formation of branched hydrocarbons and also lower molecular weight hydrocarbons, thereby improving the quality of diesel boiling-range hydrocarbons in terms of reducing pour point and cloud point, and improving the quality of gasoline boiling-range hydrocarbons in terms of increasing octane number. The results of the batch tests conducted using this catalyst are summarized in Table 2 below, which includes the recovered product composition, following conversion of the wax.

TABLE 2

Conversion of Wax in Batch Testing with Ga-ZSM-5 Catalyst

| Temperature, ° C. | 303-342 | 326-335 | 299-315 |
|---|---|---|---|
| Flowing gas | $H_2$ | $H_2$ + CO synthesis gas | $H_2$ |
| Time of test, min | 65 | 135 | 210 |
| Wax converted | 100% | 100% | 100% |
| Recovered Liquid composition | $C_3$-$C_{26}$ | $C_3$-$C_{26}$ | $C_3$-$C_{26}$ |
| Hydrocarbon Types | | | |
| paraffins, wt-% | 19.3 | 15.8 | 16.7 |
| isoparaffins, wt-% | 46.3 | 46.3 | 53.4 |
| naphthenes, wt-% | 9.2 | 8.1 | 8.9 |
| aromatics, wt-% | 17.2 | 17.7 | 14.4 |
| olefins, wt-% | 7.9 | 11.8 | 6.7 |
| Research Octane Number | 78.9 | 79.9 | 79.7 |
| Hydrocarbon Boiling-Range Fractions | | | |
| wt-% gasoline | 87.4 | 84.4 | 75.1 |
| wt-% jet | 10.3 | 12.1 | 21.5 |
| wt-% heavy diesel | 2.1 | 2.9 | 3.2 |
| wt-% total diesel | 12.6 | 15.0 | 24.7 |
| wt-% VGO | .2 | .2 | .2 |

These tests clearly demonstrated that the Ga-ZSM-5 catalyst can result in significant hydroisomerization and hydrocracking of the wax, such that the product following this finishing step, undertaken after the FT synthesis reaction, can be blended with crude oil and transported. The use of a separate finishing reactor to convert wax is superior to other proposed options to date, including the use of a wax conversion catalyst within the FT reactor.

Example 5

Improvement in FT Product Quality, Due to Finishing Stage

A material balanced "baseline FT" process was evaluated against the same process, but with the added finishing step for the hydroisomerization and hydrocracking of the wax produced in FT, according to information obtained from Example 4 above. The baseline FT process utilized a catalyst containing 20 wt-% cobalt on an alumina support, and this process was conducted for a sufficiently long period to establish operational equilibrium, particularly with respect to the wax formation rate. A finishing reactor containing the Ga-ZSM-5 finishing catalyst as described in Example 4 was added downstream of the baseline FT process, to evaluate its ability to convert the FT wax produced in the baseline FT process and thereby improve overall product quality, relative to the use of the baseline FT process alone. This improvement is illustrated in Table 3 below.

TABLE 3

Improvement in FT Product Quality, Resulting from Wax Conversion (Finishing)

| | Baseline FT | FT plus Wax Conversion |
|---|---|---|
| FT synthesis reaction temperature, ° C. | 216 | 216 |
| pressure, MPa | 2.07 | 2.07 |
| finishing reaction temperature, ° C. | N/A | 260 |
| wt-% material recovery | 96 | 100 |
| wt-% carbon recovery | 95 | 96 |
| % CO conversion | 56 | 53 |
| % C selectivity to $C_1$-$C_3$ hydrocarbons | 36 | 40 |
| % C selectivity to $C_4^+$ liquid hydrocarbons | 26 | 60 |
| % C selectivity to wax | 39 | 0 |

In view of these results, it can be seen that the combined FT synthesis and finishing stages result in the production of no wax, i.e., no hydrocarbons having melting points above room temperature. Also, by adding the finishing stage with the Ga-ZSM-5 catalyst, the selectivity to hydrocarbons useful for liquid fuels (such as $C_4$-$C_{19}$ liquid hydrocarbons), i.e., the percentage of carbon in CO converted by FT synthesis that resulted in these hydrocarbons, was increased. The selectivity to $C_1$-$C_3$ gaseous hydrocarbons was also slightly increased, as a result of cracking reactions that generated these products. Although these tests were not optimized in terms of minimizing the $C_1$-$C_3$ gaseous hydrocarbon yield and maximizing the liquid hydrocarbon fuel yield, they nonetheless demonstrated that the use of the finishing (hydroisomerization and hydrocracking) reactions can convert essentially all of the wax to condensable liquid hydrocarbons useful as fuels, without an excessive generation of gaseous hydrocarbons. The complete conversion of wax was confirmed by gas chromatography-mass spectrometry analysis (GC-MS) of the finishing product obtained after the finishing reaction.

Example 6

Integration with Biomass Hydropyrolysis to Improve Biogenic Liquid Fuel Yield

A comparison was made between the costs and performance of the hydropyrolysis process depicted in FIG. 6 and the process in which an integrated CSR-FT process is added, as depicted in FIG. 5, to increase the yield of biogenic liquid fuels from a biomass-containing feedstock (wood). The evaluation of each case was based on a 500 ton per day (t/d) production rate of liquid fuels, for calculation purposes. This comparison is provided in Table 4 below.

TABLE 4

Advantage of CSR-FT Integration with Hydropyrolysis

|  | Hydropyrolysis alone | Hydropyrolysis, Integrated with CSR-FT |
|---|---|---|
| Liquid fuel yield, based on biomass, wt-% | 26 | 38 |
| Natural gas input, based on biomass, wt-% | 0 | 14 |
| Capital cost estimate, millions $ | 179 | 227 |
| Utilities, megawatt | 2.0 | 2.0 |
| Makeup water, liters/sec | 17.9 | 17.9 |
| Wastewater out, liters/sec | 7.1 | 7.1 |

It can be seen from this comparison that the addition of an integrated CSR-FT process, to produce additional hydrocarbons from the hydropyrolysis gaseous mixture 4 as shown in FIG. 5, provides a substantial improvement in the yield of these hydrocarbons (38 wt-% vs. 26 wt-%, based on biomass). The carbon in these additional hydrocarbons is derived from biomass, such that all liquid fuel from each case above is biogenic. It is estimated that the addition of a CSR-FT process can increase the production rate of gasoline and diesel boiling-range hydrocarbons from 86 gallons per ton of wood biomass to 120 gallons per ton.

Overall, aspects of the invention relate to the use of dry reforming or $CO_2$-steam reforming to achieve high conversion of methane and/or other hydrocarbon(s) and produce a synthesis gas product having desired characteristics, including molar $H_2$:CO ratios as described herein. Further aspects relate to such reforming processes that use an active reforming catalyst with the ability to convert methane and/or other hydrocarbon(s) in the presence of $CO_2$, or both $CO_2$ and $H_2O$, with little coke deposition and high catalyst stability, even in the case of feeds comprising sulfur-bearing contaminants and/or reactive compounds such as aromatic and/or olefinic hydrocarbons, with such contaminants and compounds being associated with rapid deactivation in conventional catalyst systems. Yet further aspects relate to such reforming processes that also provide a straightforward approach for direct use with further processing stages, such as Fischer-Tropsch synthesis for the production of liquid ($C_4$) hydrocarbons and/or alcohols, alcohol synthesis via fermentation, or hydrogen production. Advantageously, the processes can utilize existing $CO_2$ present in sources of both renewable and non-renewable methane, preferably without the removal of this $CO_2$, and/or can utilize lower levels of water compared to conventional steam reforming of methane. In addition, the sulfur tolerance of the reforming catalyst is further evidenced by its activity for converting sulfur-bearing contaminants into $SO_2$ and $H_2S$ that are easily managed downstream, if necessary, using a single acid gas removal step. Yet further aspects relate the integration of $CO_2$-steam reforming with Fischer-Tropsch synthesis, as described above, optionally with a finishing stage. Those having skill in the art, with the knowledge gained from the present disclosure, will recognize that various changes can be made to these processes in attaining these and other advantages, without departing from the scope of the present disclosure. As such, it should be understood that the features of the disclosure are susceptible to modifications and/or substitutions without departing from the scope of this disclosure. The specific embodiments illustrated and described herein are for illustrative purposes only, and not limiting of the invention as set forth in the appended claims.

The invention claimed is:

1. A process for producing $C_4^+$ hydrocarbons, the process comprising:
    (a) in a reforming stage, contacting a gaseous mixture comprising methane and an oxidant with a reforming catalyst to produce a synthesis gas product;
    (b) converting, in a Fischer-Tropsch (FT) reactor, $H_2$ and CO in the synthesis gas product to hydrocarbons, including the $C_4^+$ hydrocarbons, provided in an FT product of the FT reactor; and
    (c) feeding the FT product, including the $C_4^+$ hydrocarbons, to a finishing reactor to convert at least about 75% of normal $C_{20}^+$ hydrocarbons in a wax fraction of the FT product to $C_4$-$C_{19}$ hydrocarbons,
    wherein the reforming catalyst comprises Pt in an amount from 0.05% to 5% by weight of the catalyst, on a solid support comprising cerium oxide in an amount of at least 80% by weight of the solid support.

2. A process for producing $C_4^+$ hydrocarbons, the process comprising:
    (a) in a reforming stage, contacting a gaseous mixture comprising methane and an oxidant with a reforming catalyst to produce a synthesis gas product;
    (b) converting, in a Fischer-Tropsch (FT) reactor, $H_2$ and CO in the synthesis gas product to hydrocarbons, including the $C_4^+$ hydrocarbons, provided in an FT product of the FT reactor; and
    (c) contacting a finishing feed, comprising all or a portion of the FT product, with a dewaxing catalyst in a finishing reactor to convert normal $C_{20}^+$ hydrocarbons in a wax fraction of the FT product to $C_4$-$C_{19}$ hydrocarbons by hydroisomerization and/or hydrocracking reactions;
    wherein the hydroisomerization and/or hydrocracking reactions consume hydrogen that is unconverted in the FT reactor and present in the finishing feed, and
    wherein no supplemental hydrogen source is added to the finishing reactor.

3. The process of claim 2, wherein the hydrogen that is unconverted in the FT reactor, is present in the finishing feed at a concentration of at least about 20 mol-%.

4. A process for producing $C_4^+$ hydrocarbons, the process comprising:
    (a) in a reforming stage, contacting a gaseous mixture comprising methane and an oxidant with a reforming catalyst to produce a synthesis gas product;
    (b) converting, in a Fischer-Tropsch (FT) reactor, $H_2$ and CO in the synthesis gas product to hydrocarbons, including the $C_4^+$ hydrocarbons, provided in an FT product of the FT reactor; and
    (c) in a finishing stage contacting a finishing feed, comprising all or a portion of the FT product, with a dewaxing catalyst in a finishing reactor to convert, in the finishing stage normal $C_{20}^+$ hydrocarbons in a wax fraction of the FT product to $C_4$-$C_{19}$ hydrocarbons by hydroisomerization and/or hydrocracking reactions;
    wherein the finishing feed comprises CO that is unconverted in the FT reactor.

5. The process of claim 4, wherein step (c) provides a finishing product exiting the finishing reactor and the process further comprises separating the finishing product to provide (i) $C_1$-$C_3$ hydrocarbons and residual $H_2$, CO, and $CO_2$, and (ii) liquid fuels comprising said $C_4$-$C_{19}$ hydrocarbons.

6. The process of claim 5, further comprising separating the liquid fuels into fractions comprising gasoline boiling-range hydrocarbons and diesel boiling-range hydrocarbons.

7. The process of claim 4, wherein FT reaction conditions in the FT reactor include a temperature from about 193° C. (380° F.) to about 260° C. (500° F.), a gauge pressure from about 689 kPa (100 psig) to about 3.44 MPa (500 psig).

8. The process of claim 5, wherein, in step (b), a conversion of said CO in the FT reactor is at least about 30%.

9. A process for producing $C_4^+$ hydrocarbons, the process comprising:
converting, in a Fischer-Tropsch (FT) reactor, $H_2$ and CO in a synthesis gas product to hydrocarbons, including the $C_4^+$ hydrocarbons, provided in an FT product of the FT reactor; and
in a finishing stage, feeding a finishing feed comprising all or a portion of the FT product, including the $C_4^+$ hydrocarbons and further including unconverted CO from the FT reactor, to a finishing reactor to convert, in the finishing stage, at least about 75% of normal $C_{20}^+$ hydrocarbons in a wax fraction of the FT product to $C_4$-$C_{19}$ hydrocarbons and provide a finishing product, wherein the finishing feed further includes unconverted $H_2$ from the FT reactor, said unconverted $H_2$ being present in the finishing feed at a concentration of at least about 20 mol-%.

10. The process of claim 9, wherein the synthesis gas product is obtained from contacting a gaseous mixture comprising $CO_2$ with a catalyst.

11. The process of claim 9, wherein the finishing feed comprises at least 95% of the FT product.

12. The process of claim 9, wherein a CO conversion in the FT reactor is from about 20% to about 99%, and said unconverted CO in the finishing feed represents from about 1% to about 80% of CO in the synthesis gas product.

13. The process of claim 12, wherein the CO conversion in the FT reactor is from about 30% to about 95%, and said unconverted CO in the finishing feed represents from about 5% to about 70% of CO in the synthesis gas product.

14. The process of claim 12, wherein, in the synthesis gas product, a combined concentration of $H_2$ and CO is from about 35 mol-% to about 85 mol-% and a molar $H_2$:CO ratio is from about 1.5:1 to about 2.3:1.

15. The process of claim 9, wherein said all or portion of the FT product is heated prior to said feeding to said finishing reactor.

16. The process of claim 9, wherein the finishing reactor contains a finishing catalyst having activity for hydrocracking and/or hydroisomerization of said normal $C_{20}^+$ hydrocarbons.

17. The process of claim 9, wherein the finishing product comprises less than about 2 wt-% of hydrocarbons that are solid at room temperature.

18. The process of claim 9, further comprising combining a recycle portion of the finishing product with the finishing feed or feeding the recycle portion to the finishing reactor.

19. The process of claim 4, wherein the finishing reactor is incorporated into the FT reactor.

20. The process of claim 19, wherein a bed of finishing catalyst is positioned downstream of a bed of FT catalyst, within a single vessel.

21. The process of claim 4, wherein the FT product is not separated from an outlet of the FT reactor to an inlet of the finishing reactor.

22. The process of claim 1, wherein no supplemental source of hydrogen is added to the finishing reactor.

23. The process of claim 4, wherein the oxidant comprises $CO_2$ or $H_2O$.

24. The process of claim 23, wherein the oxidant comprises a mixture of both $CO_2$ and $H_2O$.

25. The process of claim 4, wherein step (b) is carried out with an FT feed having a substantially same molar $H_2$:CO ratio as in the synthesis gas product, produced in step (a).

26. The process of claim 4, wherein, prior to step (b), water is condensed from the synthesis gas product, produced in step (a).

27. The process of claim 4, wherein step (c) is carried out in the finishing reactor at a temperature from about 232° C. (450° F.) to about 399° C. (750° F.) and a gauge pressure from about 2.00 MPa (290 psig) to about 3.10 MPa (450 psig).

28. The process of claim 4, wherein the $C_4^+$ hydrocarbons, including the $C_4$-$C_{19}$ hydrocarbons, are provided in a hydroisomerization/hydrocracking product of the finishing reactor, said hydroisomerization/hydrocracking product comprising less than about 1 wt-% hydrocarbons that are solid at room temperature.

29. The process of claim 4, wherein the finishing reactor comprises a dewaxing catalyst having hydroisomerization and/or hydrocracking activity with respect to said normal $C_{20}^+$ hydrocarbons.

30. The process of claim 29, wherein the dewaxing catalyst comprises a dewaxing active metal deposited on a solid acidic support.

31. The process of claim 30, wherein the dewaxing active metal is selected from Group 13 or Group 14 of the Periodic Table.

32. The process of claim 31, wherein the dewaxing active metal selected from Group 13 or Group 14 of the Periodic Table is present in an amount from about 0.1 wt-% to about 3 wt-%, based on the weight of the dewaxing catalyst.

33. The process of claim 32, wherein the dewaxing catalyst comprises from about 0.1 wt-% to about 3 wt-% gallium, and the solid acidic support comprises ZSM-5.

34. The process of claim 31, wherein the dewaxing active metal is gallium.

* * * * *